(12) United States Patent
Segev

(10) Patent No.: US 6,335,432 B1
(45) Date of Patent: Jan. 1, 2002

(54) STRUCTURAL ANALOGS OF AMINE BASES AND NUCLEOSIDES

(75) Inventor: David Segev, Mazkeret Batya (IL)

(73) Assignee: Bio-Red Laboratories, Inc., Hercules, CA (US)

(*) Notice: Subject to any disclaimer, the term of this patent is extended or adjusted under 35 U.S.C. 154(b) by 0 days.

(21) Appl. No.: 09/130,373

(22) Filed: Aug. 7, 1998

(51) Int. Cl.$^7$ .................................................. C07H 21/00
(52) U.S. Cl. ..................................... 536/22.1; 536/25.3
(58) Field of Search .......................... 435/6; 436/501; 536/23.1, 22.1, 24.1, 24.3, 24.33, 25.3; 935/77, 78

(56) References Cited

PUBLICATIONS

Itahara, Chemistry Letters, vol. 1986, pp. 239–242.

*Primary Examiner*—Ardin H. Marschel

(57) ABSTRACT

A compound of a general structure:

$$D—B—M$$

wherein:
- B is selected from the group consisting of derivatives of naturally occurring nitrogenous bases having a C—H group at positions 5 or 8, and derivatives of nitrogenous base-analogs having a C—H group at positions 5 or 8;
- D is at least one derivatizing group, including hydrogen; and
- M is a maleimide derivative.

40 Claims, 7 Drawing Sheets

STRUCTURAL ANALOGS OF AMINE BASES AND NUCLEOSIDES

FIELD AND BACKGROUND OF THE INVENTION

The present invention relates to fluorescent structural analogs of the non-fluorescent nucleobases (amine bases, nitrogenous bases) and nucleosides commonly found in DNA and RNA, methods of their derivatization and subsequent use thereof use in the chemical or enzymatic synthesis of fluorescent oligonucleotides (polynucleotides), and to their new and useful application as probes in hybridization and sequencing reactions and the like. Additionally, the present invention relates to applications in which fluorescent structural analogs are substituted for specific non-fluorescent nucleosides in prescribed DNA or RNA sequences and to methods of using fluorescent oligonucleotides as hybridization reagents and probes for diagnostic and therapeutic purposes and as diagnostic and therapeutic research tools. More particularly, the present invention relates to maleimide derivatives of pyrimidines such as uridine and cytidine at their C-5 position, and to maleimide derivatives of purines such as adenine and guanine at their 8-position and to methods of their synthesis and the structure and synthesis of nucleoside tri-phosphates and phosphoramidites, etc., incorporating these derivatives.

The six commonly occurring N-nucleosides which predominate in the composition of DNA and RNA from all sources have the structures:

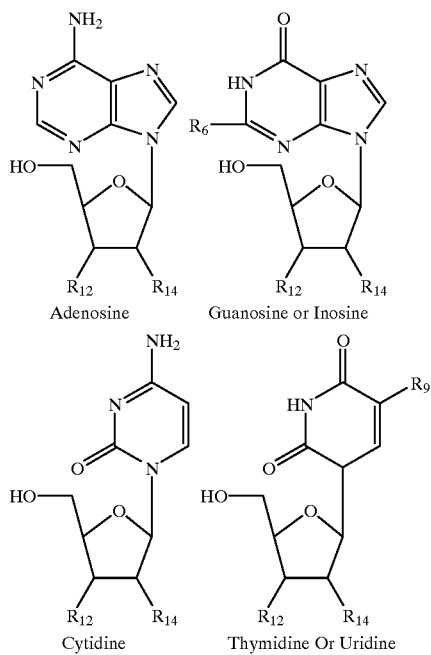

wherein $R_6$ is H for inosine and $NH_2$ for guanosine, $R_9$ is H for uridine and $CH_3$ for thymidine. Furthermore, $R_{12}$, $R_{14}$=OH for ribonucleotides, $R_{12}$=OH, $R_{14}$=H for 2'-deoxy nucleotides, $R_{12}$=H, $R_{14}$=OH for 3'-deoxy nucleotides, and $R_{12}$, $R_{14}$=H in dideoxy nucleotides.

The six commonly occurring nucleotides do not absorb light at wavelengths>290 nm and are effectively non-fluorescent under physiological conditions. Derivatives of the commonly occurring N-nucleotides for a variety of synthetic, diagnostic, and therapeutic purposes are common, including substitutions on both the heterocyclic base and the furanose ring. These substitutions can be made at the loci shown in:

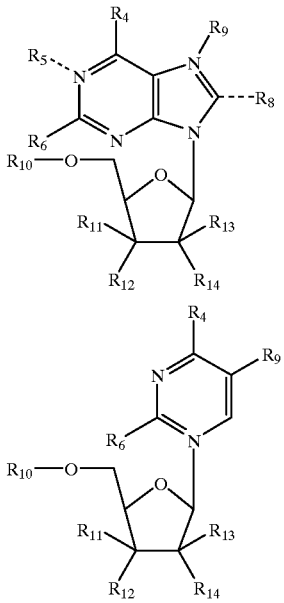

in which $R_4$ is a reactive group derivatizible with a detectable label ($NH_2$, SH,=O, and which can include an optional linking moiety including, but not limited to, an amide, thioether, or disulfide linkage or a combination thereof with additional variable reactive groups, $R_1$ through $R_3$, e.g., $R_1$—$(CH_2)_x$—$R_2$, or $R_1$—$R_2$—$(CH_2)_x$—$R_3$—, where x is an integer in the range of 1 and 25 inclusive; and $R_1$, $R_2$, and $R_3$ can be a H, OH, alkyl, acyl, amide, thioether, or disulfide); $R_5$ is H or part of an etheno linkage with $R_4$; $R_6$ is H, $NH_2$, SH, or=O; $R_9$ is hydrogen, methyl, bromine, fluorine, or iodine, or an alkyl or aromatic substituent, or an optional linking moiety including an amide, thioether, or disulfide linkage or a combination thereof such as $R_1$—$(CH_2)_x$—$R_2$, or $R_1$—$R_2$—$(CH_2)_x$—$R_3$—, where x is an integer in the range of 1 and 25 inclusive; $R_{10}$ is hydrogen, or an acid-sensitive base stable blocking group, or a phosphorous derivative, $R_{11}$=$R_{12}$=H; $R_{12}$ is hydrogen, OH, or a phosphorous derivative; R is H, OH or OR where R is a protecting group or additional fluorophore. The letters N and C in the N-nucleosides and C-nucleosides designate the atom at which the glycosidic covalent bond connects the sugar and the heterocyclic base. In the cases of the commonly occurring nucleosides, the bases are either adenine, guanine, cytosine, inosine, uracil, or thymine. The bases are attached to a furanose sugar, a general structure of which is shown hereinunder.

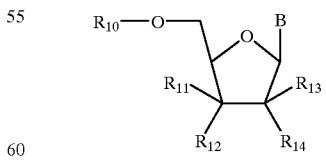

The sugar substituents for the fluorescent analogs share the same numbering system for all R groups, but the numbering system for some of the heterocycle analogs may differ.

Nucleotide sequences are commonly utilized in a variety of applications including diagnostic and therapeutic probes which hybridize target DNA and RNA and amplification of target sequences. It is often necessary, or useful, to label nucleotide sequences.

Labeling of oligonucleotide probes with radioisotopes. Hybridization of specific DNA or RNA sequences typically involves annealing oligonucleotides of lengths which range from as little as 5 bases to more than 10,000 bases (10 kb). The majority of oligonucleotide probes is currently in research use are radioactively labeled; however, because of (i) the short half lives of the isotopes in common usage, (ii) the safety requirements, and (iii) the costs of handling and disposal of radioactive probes, convenient and sensitive non-isotopic methods of detection are required for hybridization diagnostic methods to achieve widespread acceptance and application.

Non-isotopic methods of labeling oligonucleotide probes. In general, all of the non-isotopic methods of detecting hybridization probes that are is currently available depend on some type of derivatization of the nucleotides to allow for detection, whether through antibody binding, or enzymatic processing, or through the fluorescence or chemiluminescence of an attached "reporter" molecule. In most cases, oligonucleotides have been derivatized to incorporate single or multiple molecules of the same reporter group, generally at specific cyclic or exocyclic positions.

Techniques for attaching reporter groups have largely relied upon (i) functionalization of 5' or 3' termini of either the monomeric nucleosides or the oligonucleotide strands by numerous chemical reactions using deprotected oligonucleotides in aqueous or largely aqueous media (see Cardullo et al. [1988] *PNAS* 85:8790–8794); (ii) synthesizing modified nucleosides containing (a) protected reactive groups, such as $NH_2$, SH, CHO, or COOH, (b) activatable monofunctional linkers, such as NHS esters, aldehydes, or hydrazides, or (c) affinity binding groups, such as biotin, attached to either the heterocyclic base or the furanose moiety. Modifications have been made on intact oligonucleotides or to monomeric nucleosides which have subsequently been incorporated into oligonucleotides during chemical synthesis via terminal transferase or "nick translation" (see, e.g., Brumbaugh et al. [1988] *PNAS* 85:5610–5614; Sproat, B. S., A. L. Lamond, B. Beijer, P. Neuner, P. Ryder [1989] *Nucl. Acids Res.* 17:3371–3386; Allen, D. J., P. L. Darke, S J. Benkovic [1989] *Biochemistry* 28:4601–4607); (iii) use of suitably protected chemical moieties, which can be coupled at the 5' terminus of protected oligonucleotides during chemical synthesis, e.g., 5'-aminohexyl-3'-O-phosphoramidite (Haralambidis, J., L Duncan, G. W. Tregar [1990] *Nucl. Acids Res.* 18:493–499); and, (iv) addition of functional groups on the sugar moiety or in the phosphodiester backbone of the polymer (see Conway, N. E., J. Fidanza, L. W. McLaughlin [19891 *Nucl. Acids Res. Symposium Series* 21:43–44; Agrawal, S., P. C Zamecnik [19901 *Nucl. Acids Res.* 18:5419–5423).

At the simplest, non-nucleoside linkers and labels have been attached to the 3' or 5' end of existing oligonucleotides by either enzymatic or chemical methods. Modification of nucleoside residues internal to the sequence of a DNA or RNA strand has proven to be a difficult procedure, since the reaction conditions must be mild enough to leave the RNA or DNA oligomers intact and still yield reaction products which can participate in normal Watson-Crick base pairing and stacking interactions.

Derivatizations of the heterocyclic base. Numerous methods for both cyclic and exocyclic derivatization of the N-nucleoside base have been described, including the following:

(i) Hapten labeling. DNA probes have been amino modified and subsequently derivatized to carry a hapten such as 2,4-dinitrophenol (DNP) to which enzyme-conjugated anti-hapten antibodies bind which subsequently can be processed using a calorimetric substrate as a label (Keller et al. [1988] *Analytical Biochemistry* 170:441–450).

(ii) Amino- and thiol-derivatized oligonucleotides. Takeda and lkeda ([1984] *Nucl. Acids Research Symposium Series* 15:101–104) used phosphotriester derivatives of putresceinyl thymidine for the preparation of amino-derived oligomers. Ruth and colleagues have described methods for synthesizing a deoxyuridine analog with a primary amine "linker arm" 12 carbons in length at $C_5$ (Jablonski et al. [1986] *Nucl. Acids Res.* 14:6115–6128). These were later reacted with fluorescein to produce a fluorescent molecule. Urdea and Horn were granted a patent in 1990 (U.S. Pat. No. 4,910,300) covering pyrimidine derivatives on which the 6-amino group at $C_4$ had bee n modified. 3' and 5' amino modfying phosphoramidites have been widely used in chemical synthesis or derivatized oligonucleotides and are commercially available (iii) Labeling with photobiotin and other biotinylating agents. The high affinity of biotin for avidin has been used to bind enzymatic or chemiluminescent reagents to derivatized DNA probes (Foster et al. [1985] *Nucl. Acids Res.* 13:745–761). Biotin conjugated to other linkers has also been widely used, including biotin-NHS esters (Bayer, E. A., M. Wilchek [1980] *Methods in Biochemical Analysis* 26:1), biotin succinamides (Lee, W. T., D. H. Conrad [1984] *J Exp. Med.* 159:1790), and biotin maleimides (Bayer, E. A. et al. [1985] *Anal. Biochem* 149:529). Reisfeld et al. ([1987] *BBRC* 142:519–526) used biotin hydrazide to label the 4-amino group of cytidine. A patent was granted to Klevan et al. in 1989 (U.S. Pat. No. 4,828,979) for such derivatizations at the 6-position of adenine, the 4-position of cytosine, and the 2-position of guanine. These derivatizations interfere with hydrogen bonding and base-pairing and have limited uses in producing oligomers for use in hybridization.

(iv) dU-Biotin labeling. Nucleoside 5'-triphosphates or 3'-O-phosphoramidites were modified with a biotin moiety conjugated to an aliphatic amino group at the 5-position of uracil (Langer et al. [1981] *PNAS* 78:6633–6637; Saiki et al. [1985] *Science* 230:1350–1354). The nucleotide triphosphate derivatives are effectively incorporated into double stranded DNA by standard techniques of "nick translation". Once in an oligonucleotide, the residue may be bound by avidin, streptavidin, or anti-biotin antibody which can then be used for detection by fluorescence, chemiluminescence, or enzymatic processing.

(v) 11-digoxigenin-ddUTP labeling. The enzyme, terminal transferase, has been used to add a single digoxigenin-11-dideoxyUTP to the 3' end of oligonucleotides. Following hybridization to target nucleic acids, DIG-ddUTP labeled hybridization probes were detected using anti-DIG antibody conjugate.

(vi) Immunofluorescent detection. Immunofluorescent detection can be done using monoclonal Fab' fragments which are specific for RNA:DNA hybrids in which the probe has been derivatized with, e.g., biotin-11-UTP (Bobo et al. [1990] *J. Clin. Microbiol.* 28:1968–1973; Viscidi et al. [1986] *J. Clin. Microbiol.* 23:311–317).

(vii) Bisulfite modification of cytosine. Draper and Gold ([1980] *Biochemistry* 19:1774–1781) introduced aliphatic amino groups onto cytidine by a bisulfite catalysed termination reaction; the amino groups were subsequently labeled with a fluorescent tag. In this procedure, the amino group is attached directly to the pyramid base. Like the derivatization of uracil, these derivatizations interfere with hydrogen bonding and base-pairing and are not necessarily useful for producing efficient hybridization oligomers.

(viii) Fluorophore derivatized DNA probes. Texas Red (Sulfochloro-Rhodamine) derivatized probes are commercially available which hybridize to specific target DNAs and which can be detected using a flow cytometer or a microscope. Numerous authors have reported coupling fluorophores to chemically synthesized oligonucleotides which carried a 5' or 3' terminal amino or thiol group (Brumbaugh et al. [1988] Nucl. Acids Res. 16:4937–4956).

(ix) Direct enzyme labeling. Chemical coupling of an enzyme directly to a chemically synthesized probe has been used for direct detection through substrate processing. For example, Urdea et al. described an oligonucleotide sandwich assay in which multiple DNA probe hybridizations were used to bind target DNA to a solid phase after which it was further labeled with additional, alkaline phosphatase-derivatized hybridization probes (Urdea et al. [1989] Clin. Chem 35:1571–1575).

(x) Acridinium ester labeling. A single phenyl ester of methyl acridinium is attached at a central position on an RNA or DNA probe. Hydrolysis of the ester releases an acridone, $CO_2$, and light. Because the ester on unhybridized probes hydrolyses more quickly than the ester on probes which have hybridized to target RNA or DNA, the chemiluminescence of the hybridized probes can be distinguished from that of free probes and is used in a "hybridization protection assay" (Weeks et al. [1983] Clin. Chem. 29:1474–1479).

Derivatizations of the furanose ring. Methods for derivatization of the furanose ring ($R_{11}$ through $R_{14}$ hereinabove) and at the phosphodiester backbone of oligonucleotides ($R_{10}$ hereinabove) have been reported.

(i) Internucleotide linkage reporter groups ($R_{10}$ site). Phosphorothioate esters have been used to provide a binding site for fluorophores such as monobromobimane (Conway et al. [1989] Nucl. Acids Res. Symposium Series 21:43–44). Agrawal and Zamecnik ([1990] Nucl. Acids Res. 18:5419–5423) reported methods for incorporating amine specific reporter groups (e.g., monobromobimane) and thiol specific reporter groups (e.g., fluorescein isothiocyanate) through modifying the phosphodiester backbone of DNA to phosphoramidites and phosphorothioate diesters, receptively.

(ii) Glycosidic reporter groups $R_{11}$ through $R_{14}$ sites). Smith, Fung, and Kaiser ([1989] U.S. Pat. No. 4,849,513) described syntheses for an assortment of derivatives and labels on the glycosidic moiety of nucleosides and nucleoside analogs through the introduction of an aliphatic amino group at $R_{10}$. The authors did not report or claim any uses or applications of inherently fluorescent oligonucleotides, either made chemically or enzymatically or using the fluorescent nucleoside analogs or their derivatives.

Fluorescent N-nucleosides and fluorescent structural analogs. Formycin A (generally referred to as Formycin), the prototypical fluorescent nucleoside analog, was originally isolated as an antitumor antibiotic from the culture filtrates of Nocardia interforma (Hori et al. [1966] J. Antibiotics, Ser. A 17:96–99) and its structure identified as 7-amino-3-b-D-ribofuranosyl (1H-pyrazolo-[4,3d] pyrimidine). This antibiotic, which has also been isolated from culture broths of Streptomyces lavendulae (Aizawa et al. [1965] Agr. Biol. Chem. 29:375–376), and Streptomyces gummaensis (Japanese Patent No. 10,928, issued in 1967 to Nippon Kayaku Co., Ltd.), is one of numerous microbial C-ribonucleoside analogs of the N-nucleosides commonly found in RNA from all sources. The other naturally-occurring C-ribonucleosides which have been isolated from microorganisms include formycin B (Koyama et al. [1996] Tetrahedron Lett. 597–602, Aizawa et al, supra; Umezawa et al. [1965] Antibiotics Ser. A 18:178–181), oxoformycin B (Ishizuka et al. [1968] J. Antibiotics 21:1–4; Sawa et al. [1968] Antibiotics 21:334–339), pseudouridine (Uematsu and Suahdolnik [1972] Biochemistry 11:4669–4674), showdomycin (Darnall et al. [1967] PNAS 57:548–553), pyrazomycin (Sweeny et al. [1973] Cancer Res. 33:26192623), and minimycin (Kusakabe et al. [1972] J. Antibiotics 25:44–47). Formycin, formycin B, and oxoformycin B are pyrazolopyrimidine nucleosides and are structural analogs of adenosine, inosine, and hypoxanthine, respectively; a pyrazopyrimidine structural analog of guanosine obtained from natural sources has not been reported in the literature. A thorough review of the biosynthesis of these compounds is available in Ochi et al. (1974) J. Antibiotics xxiv:909–916.

Physical properties of the N-nucleosides. Because several of the N-nucleosides were known to be active as antibiotic, antiviral, or anti-tumor compounds, their chemical derivatization and physical properties have been extensively studied and compared to the structures and syntheses of the N-nucleosides commonly found in DNA and RNA. In the late 1960s, several structural analogs of the six commonly occurring N-nucleosides were found to be fluorescent under physiological conditions; fluorescence in the analogs results from a molecular rigidity of the heterocycle structure itself; not all the structural analogs of a given type, e.g., the C-nucleosides, are fluorescent, nor is fluorescence an exclusive or inherent property of any particular class of structural analogs.

Nucleic acid hybridizations are now commonly used in genetic research, biomedical research and clinical diagnostics. In the basic nucleic acid hybridization assay, a single stranded nucleic acid (either deoxyribonucleic acid, DNA, or ribonucleic acid, RNA) is hybridized to a labeled nucleic acid probe and the resulting labeled duplexes are detected.

Chemical methods for incorporating modified nucleotides are described hereinabove and in PCT application WO 84/03285. The synthetic polynucleotides containing the modified nucleotides (usually referred as a "linker arm nucleotide") can subsequently be derivatized with a fluorescent moiety. A review of labeling oligonucleotides with a variety of fluorescent molecules is described by Kessler in Nonradioactive Labeling and Detection of Biomolecules. Springer-Verlag Berlin Heidelberg New York, (1992).

So far, nucleosides were labeled using a linker arm. No work has been described in which increasing the fluorescence of, for example, uridine and cytidine is effected by extending the conjugation of the base moieties thereof by addition of an unsaturated moiety, as further detailed hereunder.

Fluorescent dyes have many uses and are known to be particularly suitable for biological applications in which the high detectability of fluorescence is desirable. For a discussion of the revolutionary impact fluorescent dyes have had, and will continue to have, on the way research is conducted today, please refer to Taylor et al. (1992) The New Vision of Light Microscopy, American Scientist, Vol. 80, pp. 322–335.

Ideally, improvement in detecting fluorescent probes in an assay system could be obtained by selecting a fluorophore which has (i) a large Stokes shift, that is, a large separation between the wavelengths for maximum excitation (EX) and the wavelength of maximal emission (EM), e.g., EM-EX>100 nm); (ii) a high quantum yield (e.g., QY>0.5);

(iii) a high extinction coeffient (e.g., EC>30,000); and (iv) an excitation maximum close to a laser line (e.g., 442 nm of Helium-Cadmium laser or 448 nm of Argon laser).

Unfortunately, there are no common fluorophores which fully satisfy these criteria. For example, fluorescein (EX: 495 nm, EM: 525 nm, QY=0.5) is a highly fluorescent label with an excitation maximum near a laser line, but has a Stokes shift of only about 30 nm.

It is known that a larger Stokes shift can be obtained by employing a pair of donor/acceptor fluorophores which have overlapping spectra and which are arranged in close proximity for non-radiative energy transfer between the donor and acceptor fluorophores.

This form of energy transfer was proposed by Forster, who developed equations of transfer efficiency in relation to separation distances between the fluorophores. See, for example, Forster, Th., Ann. Phys. (Leipzig) 2:55–75 (1948). A more recent summary of Forster's non-radiative energy transfer is given in "Principles of Fluorescent Spectroscopy," J. R. Lakowicz, Chapt. 10 (1983). The Forster mathematical analysis predicts that the closer the spacing of the fluorescent moieties the greater the efficiency of non-radiative energy transfer therebetween. Experimental evidence confirmed this prediction.

The use of multiple fluorescent dyes in a single measurement is ever growing, however, the number of distinguishable dyes is limited. It is for this reason that sophisticated staining techniques (combinatorial labeling or hybridization) and spectral imaging devices were required to enable distinctive fluorescent painting of the 24 human male chromosomes. See, E. Schroeck et al., 1996, Multicolor spectral karyotyping of human chromosomes. Science, 273, 494–497.

There is thus a widely recognized need for, and it would be highly advantageous to have, novel fluorescent nucleobases and nucleosides, which add to the ever increasing repertoire of fluorescent dyes.

SUMMARY OF THE INVENTION

The subject invention pertains to nucleobases and nucleoside structural analogs which are fluorescent. The fluorescent nucleoside structural analogs of the present invention are useful as monomers in synthesizing and labelling nucleoside sequences (oligonucleotides, polynucleotides). When used as hybridization probes, the fluorescence of such nucleoside sequences can be used as a research or diagnostic tool to detect and identify specific genetic sequences. This methodology is distinct from other non-radioactive methods of probe detection in that it does not utilize nucleosides which have been coupled to enzymes or other reactive proteins and does not require post-hybridization processing for the detection of hybridization. In their dideoxy form, the fluorescent nucleoside structural analogs of the present invention are useful as fluorescent chain elongation terminators in DNA sequencing reactions.

Thus, the nucleoside analogs according to the present invention can be used as (i) specific substitutes for a given non-fluorescent nucleoside in an oligonucleotide or polynucleotide probe, (ii) as labels for the identification and detection of specific sequences of a template; and (iii) for nucleic acid sequencing.

It is an object of the present invention to provide novel, inherently fluorescent nucleobases and nucleoside analogs and the novel triphosphate and phosphoramidite forms thereof, which are useful in the synthesis of labelled polynucleoside probes, amplimers, diagnostics, sequencing and therapeutics.

It is a further object of the present invention to provide methods of making autofluorescencing oligonucleotides and polynucleotides capable of specific Watson-Crick base pairing with prescribed sequences of target DNA or RNA.

It is another object of the invention to provide methods of using fluorescent nucleoside analogs and oligonucleotides made therefrom and synthesized according to the methods of the present invention to identify, detect the presence of, and/or alter the function of known nucleic acid sequences of DNA and RNA.

Thus, according to the present invention there is provided a compound of a general structure:

wherein:
B is selected from the group consisting of derivatives of naturally occurring nitrogenous bases having a C—H group at positions 5 or 8, and derivatives of nitrogenous base-analogs having a C—H group at positions 5 or 8;
D is at least one derivatizing group, including hydrogen; and
M is a maleimide derivative.

According to further features in preferred embodiments of the invention described below, B is selected from the group consisting of adenine derivative, guanine derivative, uracil derivative, cytosine derivative and inosine derivative.

According to still further features in the described preferred embodiments B is selected from the group consisting of purine derivative and pyrimidine derivative.

According to still further features in the described preferred embodiments D includes a chemical functionality group attached to a linker arm.

According to still further features in the described preferred embodiments D includes a ribose derivative.

According to still further features in the described preferred embodiments D further includes one to three phosphate groups attached at a 5' position on the ribose derivative.

According to still further features in the described preferred embodiments D further includes a phosphoramidite derivative attached at a 3' position on the ribose derivative.

According to still further features in the described preferred embodiments D includes a deoxyribose derivative.

According to still further features in the described preferred embodiments D further includes one to three phosphate groups attached at a 5' position on the deoxyribose derivative.

According to still further features in the described preferred embodiments D further includes a phosphoramidite derivative attached at a 3' or 5' position on the deoxyribose derivative.

According to still further features in the described preferred embodiments D is a polymer.

According to still further features in the described preferred embodiments the polymer includes nucleoside derivatives.

According to still further features in the described preferred embodiments the polymer includes amino acid derivatives.

According to still further features in the described preferred embodiments the polymer is a polynucleotide.

According to still further features in the described preferred embodiments the polymer is a polypeptide.

According to still further features in the described preferred embodiments the polymer is a protein-nucleic acid polymer.

Further according to the present invention, there is provided a compound having a structure selected from the group consisting of:

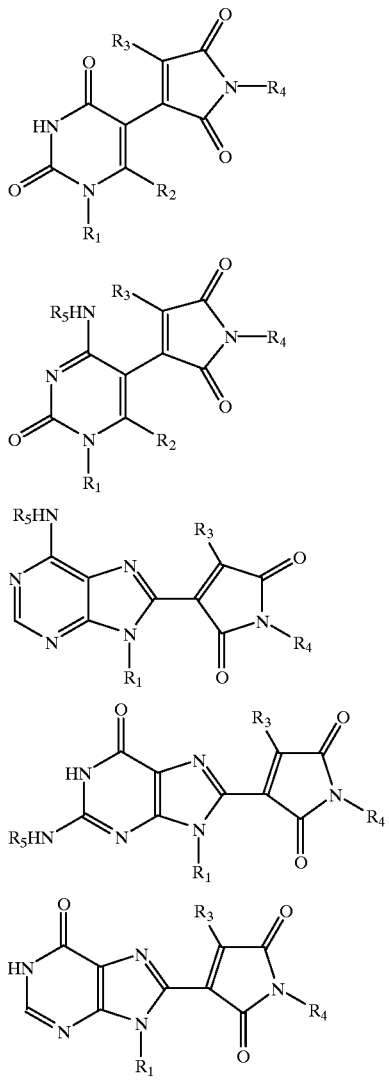

wherein:

$R_1$, $R_2$, $R_3$, $R_4$ and $R_5$ are each independently a derivatizing group, including hydrogen.

According to still further features in the described preferred embodiments $R_1$ is terminating with a reactive group having a general structure of:

$(P)_n A.$ wherein:

P is selected from the group consisting of alkyl, branched alkyl, aromatic group, derivatized aromatic group and combinations thereof;

n is an integer in a range of 1 to 100; and

A is an active chemical moiety.

According to still further features in the described preferred embodiments n is an integer in a range of 2–50.

According to still further features in the described preferred embodiments n is an integer in a range of 3–7.

According to still further features in the described preferred embodiments A is capable of reacting with a nucleophile.

According to still further features in the described preferred embodiments the nucleophile is selected from the group consisting of amino and hydroxy groups.

According to still further features in the described preferred embodiments A is designed to form a chemical bond with the nucleophile, the bond is selected from the group consisting of ether bond, ester bond, amide bond, phosphonate bond, carbamate bond, and sulfone bond.

According to still further features in the described preferred embodiments A is an active ester.

According to still further features in the described preferred embodiments the active ester is selected from the group consisting of N-hydroxy succinimido, halogenoacyl, vinylsulfone, isothiocyanate, cyanate, chloromethyl ketone, iodoacetamidyl, iodoalkyl, bromoalkyl and active phosphate group.

According to still further features in the described preferred embodiments $R_2$ and $R_3$ are each independently selected from the group consisting of hydrogen, methyl, halogen, and an unsaturated moiety having a structure:

wherein:

m is an integer in a range of 1 to 6;

Z is selected from the group consisting of hydrogen, hydroxyl, amine, amide, nitro, an electron withdrawing group, an electron attracting groups and an aromatic group terminating with the hydrogen, hydroxyl, amine, amide, nitro, an electron attracting groups.

According to still further features in the described preferred embodiments $R_4$ is selected from the group consisting of alkyl and aromatic group.

According to still further features in the described preferred embodiments $R_5$ is selected from the group consisting of hydrogen and amino protecting group useful in a protection of amino acids in peptide synthesis.

According to still further features in the described preferred embodiments the amino protecting group is selected from the group consisting of trifluoroacetyl, acetyl, benzoyl, 9-fluorenylmethyloxycarbonyl, allyloxycarbonyl, 4-toluenesulfonylethyloxycarbonyl, methylsulfonylethyloxycarbonyl, 2-cyano-t-butyloxycarbonyl, chloroacetyl, acetoacetyl and 2,2,2-trichloroethyloxycarbonyl.

Further according to the present invention there is provided a compound having a structure selected from the group consisting of:

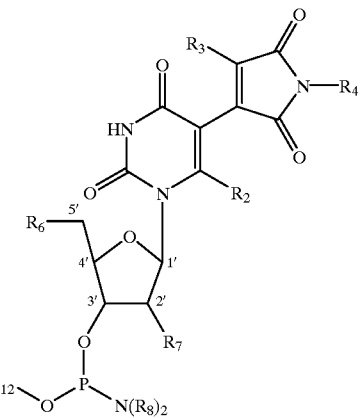

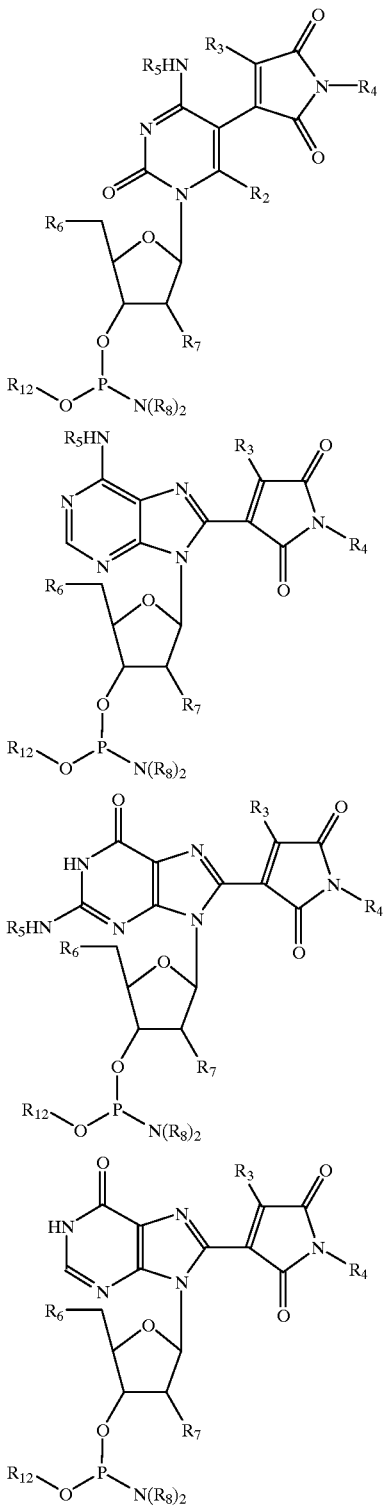

wherein:

$R_2$, $R_3$, $R_4$, $R_5$, $R_6$, $R_7$, $R_8$ and $R_{12}$, are each independently a derivatizing group.

According to still further features in the described preferred embodiments $R_6$ is a chemical functionality group.

According to still further features in the described preferred embodiments the chemical functionality group is selected from the group consisting of hydroxylic group $OR_9$ and amino group $NR_{10}$.

According to still further features in the described preferred embodiments $R_9$ is an acid labile protecting group.

According to still further features in the described preferred embodiments the acid labile protecting group is selected from the group consisting of triphenylmethyl, p-anisyldiphenylmethyl, di-p-anisyldiphenylmethyl, p-dimethoxy trityltrityl, formyl, t-butyloxycarbonyl, benzyloxycarbonyl, 2-chlorobenzyloxycarbonyl, 4-chlorobenzoyloxycarbonyl, 2,4-dichlorobenzyloxycarbonyl, furfurylcarbonyl, t-amyloxycarbonyl, adamantyloxycarbonyl, 2-phenylpropyl-(2)-oxycarbonyl, 2-(4-biphenyl)propyl-(2)-oxycarbonyl, 2-nitrophenylsulfenyl and diphenylphosphinyl.

According to still further features in the described preferred embodiments $R_9$ is a base labile protecting group.

According to still further features in the described preferred embodiments the base labile protecting group is selected from the group consisting of trifluoroacetyl, 9-fluorenylmethyloxycarbonyl, allyloxycarbonyl, 4-toluenesulfonylethyloxycarbonyl, methylsulfonylethyloxycarbonyl, 2-cyano-t-butyloxycarbonyl, silyl ethers, and, 2,2,2-trichloroethylcarbonate.

According to still further features in the described preferred embodiments $R_{10}$ is a nitrogen protecting group.

According to still further features in the described preferred embodiments the nitrogen protecting group is selected from the group consisting of trifluoroacetyl, 9-fluorenylmethyloxycarbonyl, allyloxycarbonyl 4-toluenesulfonylethyloxycarbonyl, methylsulfonylethyloxycarbonyl, and 2-cyano-t-butyloxycarbonyl, chloroacetyl, acetoacetyl, and 2,2,2-trichloroethyloxycarbonyl.

According to still further features in the described preferred embodiments $R_5$ is a chemical functionality group.

According to still further features in the described preferred embodiments the chemical functionality group is an amino group $NR_{10}$.

According to still further features in the described preferred embodiments $R_{10}$ is an acid labile protecting group.

According to still further features in the described preferred embodiments the acid labile protecting group is selected from the group consisting of triphenylmethyl, p-anisyldiphenylmethyl, di-p-anisyldiphenylmethyl, p-dimethoxytrityl, formyl, t-butyloxycarbonyl, benzyloxycarbonyl, 2-chlorobenzyloxycarbonyl, 4-chlorobenzoyloxycarbonyl, 2,4-dichlorobenzyloxycarbonyl, furfurylcarbonyl, t-amyloxycarbonyl, adamantyloxycarbonyl, 2-phenylpropyl-(2)-oxycarbonyl, 2-(4-biphenyl)propyl-(2)-oxycarbonyl, di-p-anisyldiphenylmethyl, 2-nitrophenylsulfenyl and diphenylphosphinyl.

According to still further features in the described preferred embodiments the base labile protecting group is selected from the group consisting of trifluoroacetyl, 9-fluorenylmethyloxycarbonyl, 4-toluenesulfonylethyloxycarbonyl, methylsulfonylethyloxycarbonyl and 2-cyano-t-butyloxycarbonyl.

According to still further features in the described preferred embodiments $R_7$ is selected from the group consisting of hydrogen and $OR_{11}$, wherein $R_{11}$ is a chemical protecting group.

According to still further features in the described preferred embodiments the $R_{11}$ protecting group is selected from the group consisting of lower aryl and alkylether.

According to still further features in the described preferred embodiments the $R_{11}$ protecting group is selected from the group consisting of, triphenylmethyl, acetal, tetrahydropyranyl, silyl ether, trimethylsilyl and t-butyldimethylsilyl.

According to still further features in the described preferred embodiments the $R_{11}$ protecting group is selected from the group consisting of hydroxylic and amino groups According to still further features in the described preferred embodiments $R_8$ is selected from the group consisting of lower and heterocyclic alkyl.

According to still further features in the described preferred embodiments $R_8$ is selected from the group consisting of methyl, isopropyl, morpholino, pyrrolidino and 2,2,6,6-tetramethylpyrrolidino.

According to still further features in the described preferred embodiments $R_{12}$ is a phosphate protecting group.

According to still further features in the described preferred embodiments the phosphate protecting group is selected from the group consisting of trichloroethyl, allyl, cyanoethyl and sulfonylethyl.

Further according to the present invention there is provided a compound selected from the group consisting of:

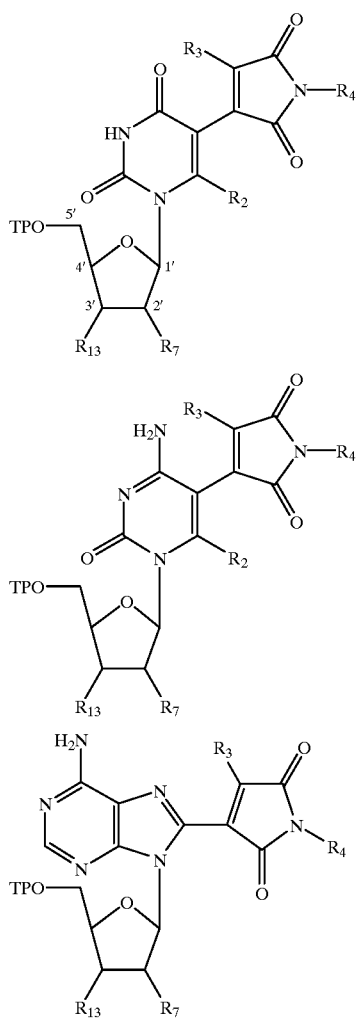

-continued

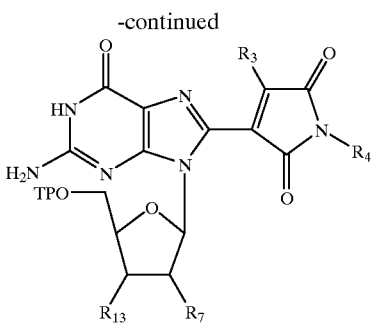

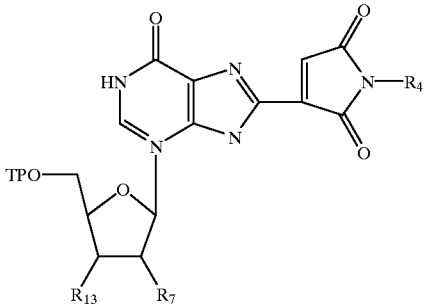

wherein TPO is a triphosphate group, $R_2$, $R_3$ and $R_4$ are each independently a derivatizing group, including hydrogen, and $R_7$ and $R_{13}$ are each independently selected from the group consisting of hydrogen and hydroxyl group.

According to still further features in the described preferred embodiments $R_2$ and $R_3$ are each independently selected from the group consisting of hydrogen, methyl, halogen, an unsaturated moiety having a structure:

$$(CH=CH)_m CH_2 Z$$

wherein:

m is an integer in a range of 1 to 6;

Z is selected from the group consisting of hydrogen, hydroxyl, amine, amide, nitro, an electron withdrawing group, an electron attracting groups and an aromatic group.

According to still further features in the described preferred embodiments $R_4$ is selected from the group consisting of alkyl and aromatic group.

Further according to the present invention there is provided a method of synthesizing a compound of a general structure:

$$D—B—M$$

wherein:

B is selected from the group consisting of derivatives of naturally occurring nitrogenous bases having a C—H group at positions 5 or 8, and derivatives of nitrogenous base-analogs having a C—H group at positions 5 or 8;

D is at least one derivatizing group, including hydrogen; and

M is a maleimide derivative;

The method comprising the steps of the method comprising the steps of contacting a derivatized base DB with mercuric acetate and condensing with N-alkylmaleimide.

Further according to the present invention there is provided a method of synthesizing a compound of a general structure:

15
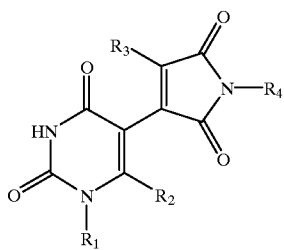
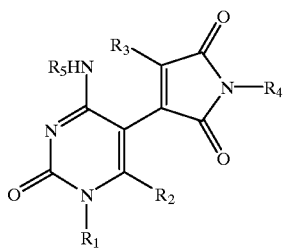
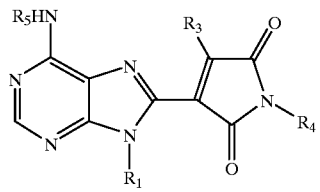
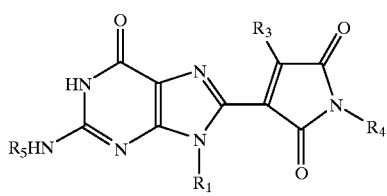
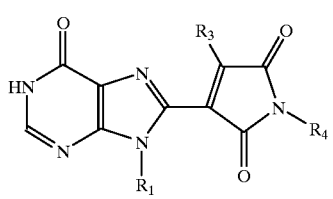
wherein:
$R_1$, $R_2$, $R_3$, $R_4$ and $R_5$ are each independently a derivatizing group, including hydrogen; the method comprising the steps of contacting a derivatized base with mercuric acetate and condensing with N-alkylmaleimide.
Further according to the present invention there is provided a method of synthesizing a compound of a general structure:
16
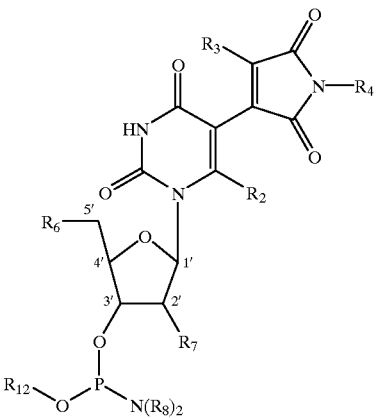
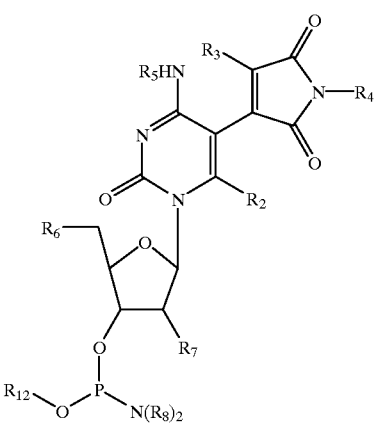
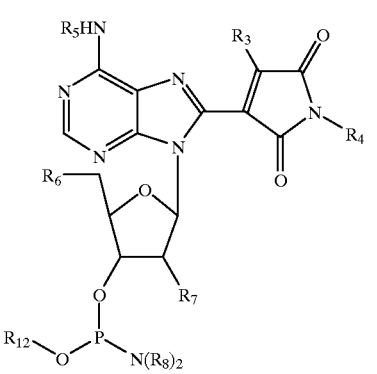
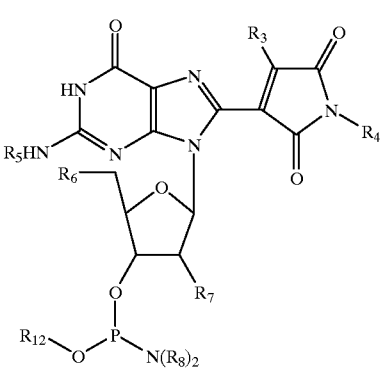

-continued

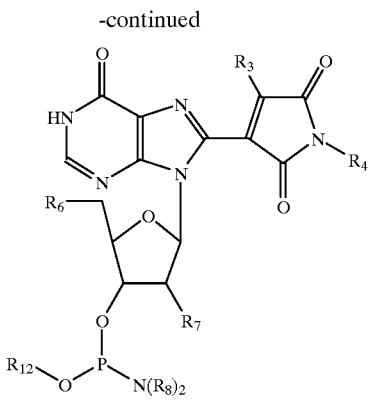

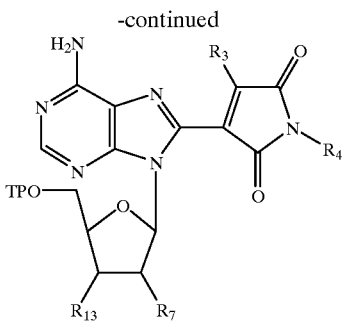

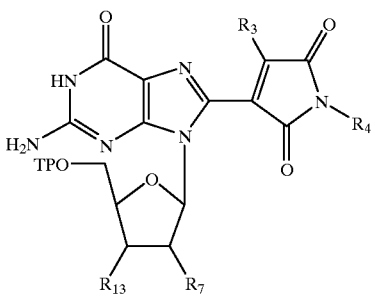

wherein $R_2$, $R_3$, $R_4$, $R_5$, $R_6$, $R_7$, $R_8$ and $R_{12}$, are each independently a derivatizing group;

The method comprising the steps of (a) contacting a nucleoside with mercuric salt, followed condensation with N-alkylmaleimide; (b) protecting amino groups of the nucleoside with a protecting group (e.g., allyloxycarbamate); (c) protecting 5' hydroxyl of the nucleoside with an acid labile group (e.g., dimethoxytrityl); and (d) condensing with allylic phosphoramidate reagent.

Further according to the present invention there is provided a method of synthesizing a compound of a general structure:

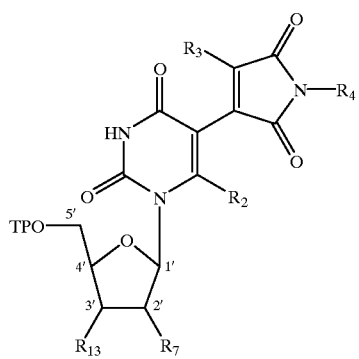

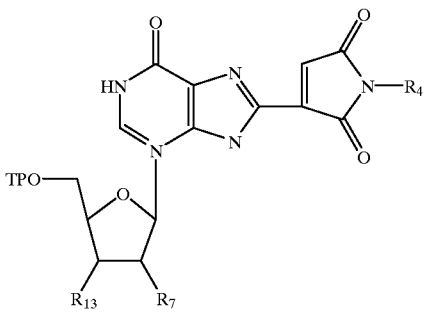

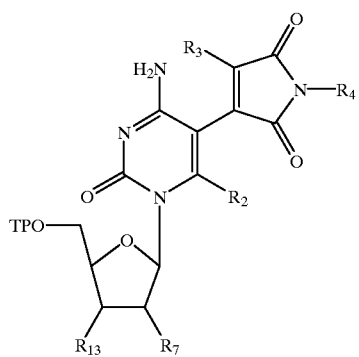

wherein TPO is a triphosphate group, $R_2$, $R_3$ and $R_4$ are each independently a derivatizing group, including hydrogen, and $R_7$ and $R_{13}$ are each independently selected from the group consisting of hydrogen and hydroxyl group; the method comprising the steps of contacting a 5' triphosphate nucleoside with mercuric salt and condensing with N-alkylmaleimide.

Further according to the present invention there is provided a method of hybridizing a target nucleic acid with a nucleic acid probe comprising the steps of contacting a sample including the target nucleic acid with the nucleic acid probe under hybridization conditions, wherein the nucleic acid probe includes at least one fluorescent derivative of a nucleobase, the fluorescent derivative includes a maleimide derivative attached at a C5 or C8 position of the nucleobase.

Further according to the present invention there is provided a method of detecting a sequence of target nucleic acid, comprising the steps of (a) providing the target nucleic acid in a single stranded form; (b) contacting, under hybridization conditions, the single stranded form of the target nucleic acid with a sequencing primer, such that a sequence dependent primer-target nucleic acid duplex is formed; and (c) contacting under polymerization conditions the duplex with deoxynucleoside-tri-phosphates and at least one dideoxynucleoside-tri-phosphate and with a DNA polymerase; wherein at least one of the sequencing primer, deoxynucleoside-tri-phosphates or the dideoxynucleoside-tri-phosphate includes a fluorescent derivative of a nucleobase, the fluorescent derivative includes a maleimide derivative attached at a C5 or C8 position of the nucleobase.

Further according to the present invention there is provided a method of synthesizing a polynucleotide comprising the steps of using a solid phase synthesis protocol to sequentially, following a predetermined order, add nucleoside derivatives present initially in their phosphoramidite form to a growing chain of the polynucleotide in a 3' to 5' direction, wherein at least one of the nucleoside derivatives includes a fluorescent derivative of a nucleobase, the fluorescent derivative includes a maleimide derivative attached at a C5 or C8 position of the nucleobase.

Further according to the present invention there is provided a method of synthesizing a polynucleotide comprising the steps of (a) providing the template nucleic acid in a single stranded form; (b) contacting, under hybridization conditions, the single stranded form of the template nucleic acid with at least one primer, such that a sequence dependent primer-target nucleic acid duplex is formed; and (c) contacting under polymerization conditions the duplex with deoxynucleoside-tri-phosphates and with a DNA polymerase; wherein at least one of the primers or the deoxynucleoside-tri-phosphates includes a fluorescent derivative of a nucleobase, the fluorescent derivative includes a maleimide derivative attached at a C5 or C8 position of the nucleobase.

Further according to the present invention there is provided a method of target dependent chemical ligation of probes comprising the steps of (a) providing a first probe including a fluorescence moiety including a is protected moiety being bound to the fluorescence moiety; (b) providing a second probe including a nucleophile moiety, the nucleophile moiety is selected such that when in appropriate proximity and orientation with respect to the protected moiety, the nucleophile moiety releases the protected moiety to yield a fluorescent moiety fluorescing or chemiluminescing differently than the fluorescence moiety; wherein the first and second probes are selected such that by hybridizing to the target the appropriate proximity and orientation are obtained.

The present invention successfully addresses the shortcomings of the presently known configurations by providing novel nucleobases and nucleoside structural analogs featuring improved spectral qualities by conjugating a maleimide derivative at C5 or C8 positions of pyrimidine nucleobases or purine nucleobases, respectively.

BRIEF DESCRIPTION OF THE DRAWINGS

The invention herein described, by way of example only, with reference to the accompanying drawings, wherein.

DESCRIPTION OF THE PREFERRED EMBODIMENTS

Figure 1:
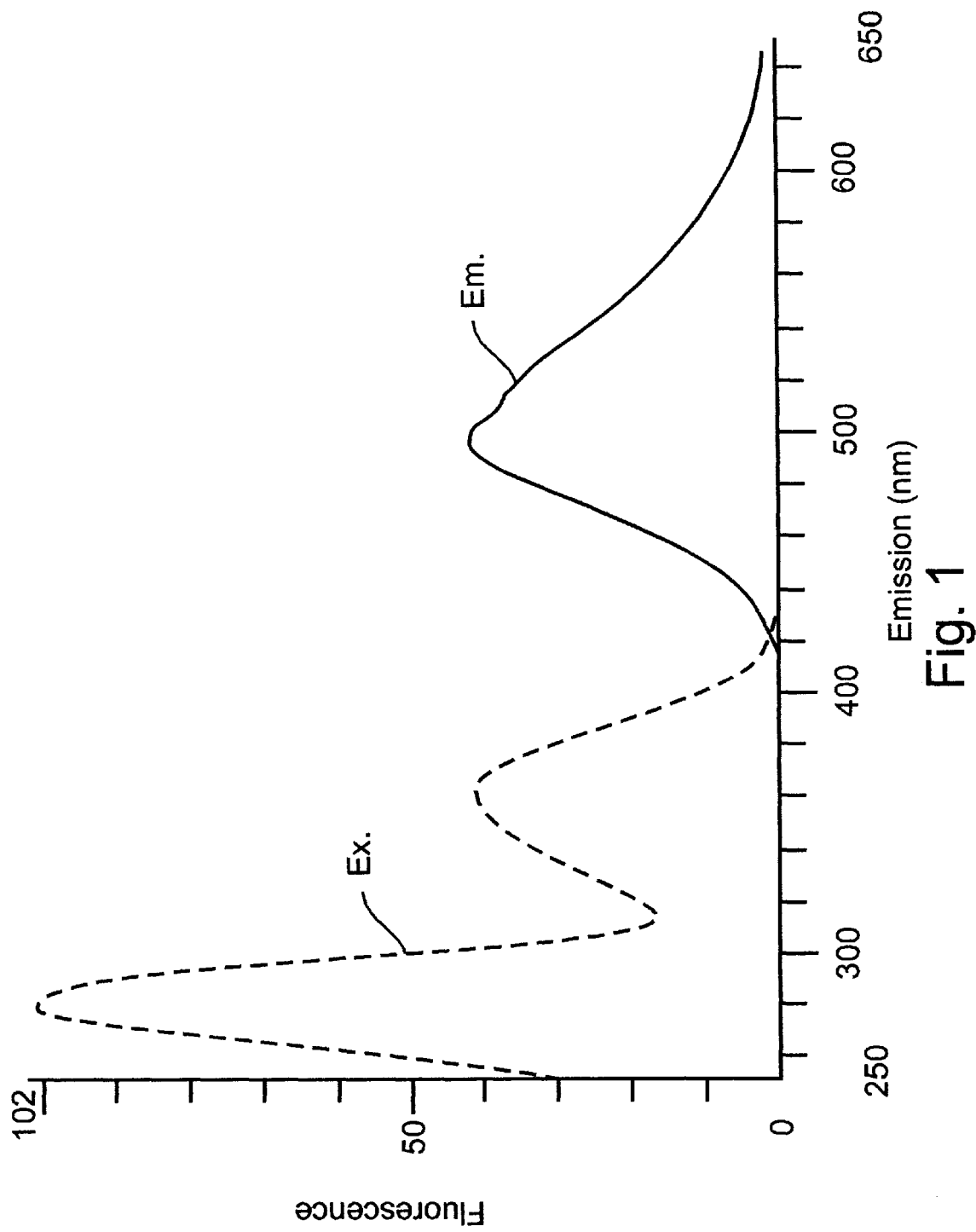
FIG. 1 is a plot showing the excitation (dotted line, Ex) and emission (solid line, Em) spectra of 2'-Deoxy-5-N-ethylmaleimidouridine dissolved in methanol (10 µg/ml) according to the present invention.

The present invention provides derivatives of pyrimidine and/or purine analogs of the commonly occurring nucleoside bases, which are fluorescent in different organic solvents and in aqueous buffers or in a mixture of organic and water solvents.

The present invention is based upon increasing the conjugation of double bonds at C-5 position of pyrimidines such as uridine and cytidine, and at C-8 position of purines of adenine and guanine. In general, as the degree of conjugation in hydrocarbon compounds increases, the intensity of fluorescence often increases and a bathochromic shift is observed. The fluorescent nucleoside or nucleotide analogs according to the present invention are useful as monomers in synthesizing and labeling nucleotide sequences and proteins.

The invention further concerns the use of these fluorescent nucleotides which can be substituted for naturally occurring nucleotides in the synthesis of oligonucleotide and polynucleotide probes. When used as hybridization probes, the fluorescence of such oligonucleotides or polynucleotides can be used as a diagnostic tool to detect and identify specific genetic sequences. This methodology is distinct from other non-radioactive methods of probe detection in that it does not utilize nucleotides which have been coupled via a linker arm to fluorescent dyes, but serves as hybridization sites and as a fluorescent dyes at the same time.

In another embodiment, the present invention provides novel fluorescent nucleoside analogs and the novel triphosphate and phosphoramidite forms thereof, which are useful in the synthesis of labeled polynucleotide probes, in branched DNA, in fluorescence in situ hybridization technology and in DNA sequencing.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

In its general form, the present invention provides a structure according to the formula:

wherein B can be a derivative of a naturally occurring nitrogenous base having a C—H group at positions 5 or 8, derivative of nitrogenous base analog having a C—H group at positions 5 or 8, preferably a purine nitrogenous base derivative or a pyrimidine nitrogenous base derivative, such as, but not limited to, an adenine derivative, guanine derivative, uracil derivative and an inosine derivative;

wherein D can be a chemical functionality group attached to a linker arm, preferably a ribose derivative, preferably derivatized with one to three phosphate groups attached at a 5' position on the ribose derivative or with a phosphoramidite derivative attached at a 3' position of the ribose derivative, a deoxyribose derivative, preferably derivatized with one to three phosphate groups attached at a 5' position on the deoxyribose derivative or with a phosphoramidite derivative attached at a 3' or 5' position of the deoxyribose derivative, a dideoxyribose derivative, preferably derivatized with three phosphate groups attached at a 5' position on the dideoxyribose derivative, a polymer, nucleoside derivative containing polymer, an amino acid derivative containing polymer, a polynucleotide, or a protein nucleic acid polymer.

In one aspect of the invention, fluorescent structural analogs Q, R, S, T, U of the commonly occurring nucleosides and their derivatives are provided having the structural formula of:

Structure Q

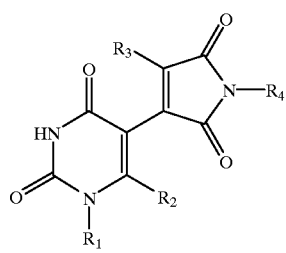

Structure R

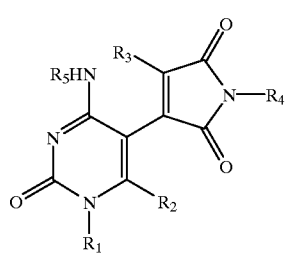

Structure S

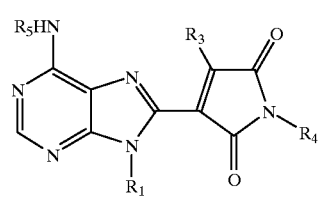

Structure T

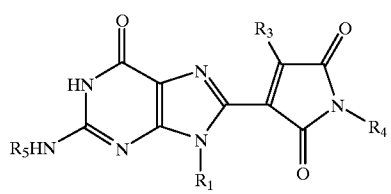

Structure U

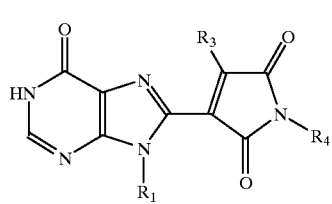

wherein structures Q, R, S, T and U contain derivatizing groups $R_1$, $R_2$, $R_3$, $R_4$ and $R_5$;

wherein $R_1$ can be alkyl and aromatic groups terminating with a reactive group having a formula $(P)_nA$;

wherein P can be alkyl, branched alkyl, aromatic group or derivatized aromatic group;

wherein n is an integer in a range of 1 to 100, preferably 2–50, most preferably 3–7; and wherein A is an active chemical moiety preferably capable of reacting with a nucleophile, amino group, hydroxy group, ester group, N-hydroxysuccininmido, halogenoacyl, vinylsulfone, isothiocyanate, cyanate, chloromethyl ketone, iodoacetamidyl, iodoalkyl, bromoalkyl, active phosphate group, etc.;

wherein $R_2$ and $R_3$ can be hydrogen, methyl halogen or an unsaturated moiety of formula:

$(CH=CH)_mCH_2Z$; 

wherein m is an integer in a range of 1–6;

wherein Z can be hydrogen, hydroxyl, amine, amide, nitro, an electron withdrawing group, an electron attracting group and an aromatic group terminating with a hydrogen, hydroxyl, amine, amide, nitro, or an electron attracting group;

wherein $R_4$ can be an alkyl or aromatic group;

wherein $R_5$ can be a hydrogen or an amino protecting group useful in the protection of amino acids in peptide synthesis, preferably trifluoroacetyl, acetyl, benzoyl, 9-fluorenylmethyloxycarbonyl, allyloxycarbonyl, 4-toluenesulfonylethyloxycarbonyl, methylsulfonylethyloxycarbonyl, 2-cyano-t-butyloxycarbonyl, chloroacetyl, acetoacetyl or 2,2,2-trichloroethyloxycarbonyl.

In another embodiment the present invention provides novel fluorescent phosphoramidite forms of nucleosides and analogs thereof, which are useful in the synthesis of fluorescently labeled polynucleotide probes. Their structures are V, W, X, Y and Z and they contain $R_2$, $R_3$, $R_4$, $R_5$, $R_6$, $R_7$, $R_8$ and $R_{12}$ derivatizing groups.

Structure V

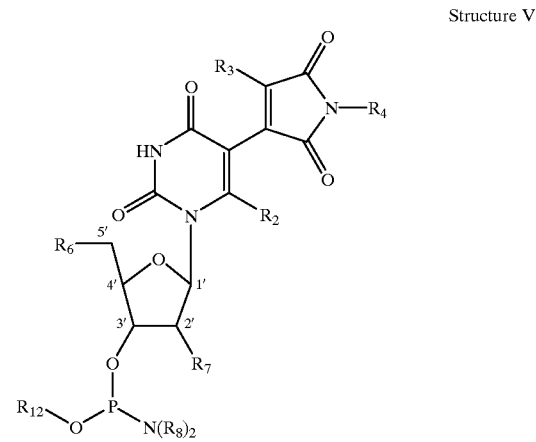

Structure W

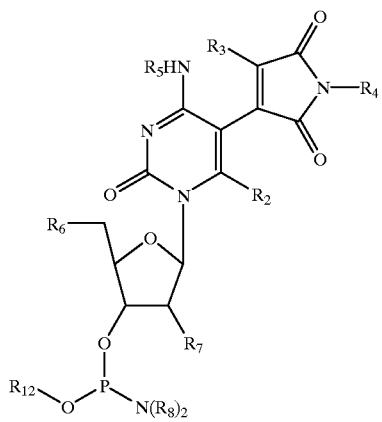

Structure X

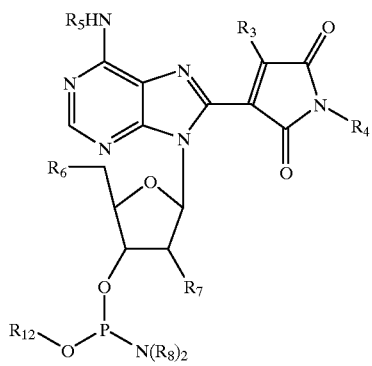

Structure Y

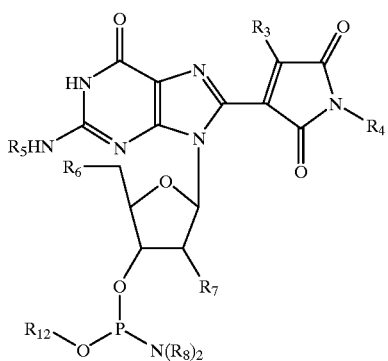

Structure Z

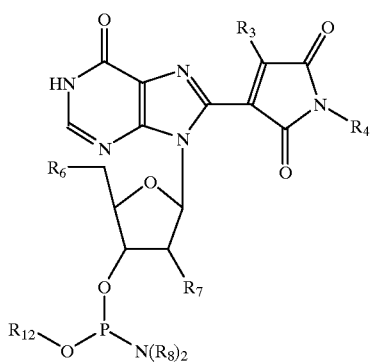

wherein $R_6$ is a chemical functionality group, preferably hydroxylic group $OR_9$ or amino group $NR_{10}$;

wherein $R_9$ is an acid labile protecting group, preferably triphenylmethyl, p-anisyldiphenylmethyl, di-p-anisyldiphenylmethyl, p-dimethoxy trityltrityl, formyl, t-butyloxycarbonyl, benzyloxycarbonyl, 2-chlorobenzyloxycarbonyl, 4-chlorobenzoyloxycarbonyl, 2,4-dichlorobenzyloxycarbonyl, furfurylcarbonyl, t-amyloxycarbonyl, adamantyloxycarbonyl, 2-phenylpropyl-(2)-oxycarbonyl, 2-(4-biphenyl) propyl-(2)-oxycarbonyl, 2-nitrophenylsulfenyl or diphenylphosphinyl;

wherein $R_9$ is a base labile protecting group, preferably trifluoroacetyl, 9-fluorenylmethyloxycarbonyl, allyloxycarbonyl, 4-toluenesulfonylethyloxycarbonyl, methylsulfonylethyloxycarbonyl, 2-cyano-t-butyloxycarbonyl, silyl ethers, or 2,2,2-trichloroethylcarbonate.

wherein $R_{10}$ is a nitrogen protecting group, preferably trifluoroacetyl, 9-fluorenylmethyloxycarbonyl, allyloxycarbonyl 4-toluenesulfonylethyloxycarbonyl, methylsulfonylethyloxycarbonyl, and 2-cyano-t-butyloxycarbonyl, chloroacetyl, acetoacetyl, or 2,2,2-trichloroethyloxycarbonyl;

wherein $R_5$ is a chemical functionality group, preferably an amino group $NR_{10}$, such as, but not limited to, triphenylmethyl, p-anisyldiphenylmethyl, di-p-anisyldiphenylmethyl, p-dimethoxytrityl, formyl, t-butyloxycarbonyl, benzyloxycarbonyl, 2-chlorobenzyloxycarbonyl, 4-chlorobenzoyloxycarbonyl, 2,4-dichlorobenzyloxycarbonyl, furfurylcarbonyl, t-amyloxycarbonyl, adamantyloxycarbonyl, 2-phenylpropyl-(2)-oxycarbonyl, 2-(4-biphenyl) propyl-(2)-oxycarbonyl, di-p-anisyldiphenylmethyl, 2-nitrophenylsulfenyl and diphenylphosphiny, or a base labile protecting group, such as, but not limited to, trifluoroacetyl, 9-fluorenylmethyloxycarbonyl, 4-toluenesulfonylethyloxycarbonyl, methylsulfonylethyloxycarbonyl and 2-cyano-t-butyloxycarbonyl;

wherein $R_7$ can be hydrogen or $OR_{11}$, wherein $R_{11}$ is a chemical protecting group, such as, but not limited to, a lower aryl or alkylether, preferably triphenylmethyl, acetal, tetrahydropyranyl, silyl ether, trimethylsilyl and t-butyl-dimethylsilyl or $R_{11}$ can be a hydroxylic or amino group;

wherein $R_8$ can be a lower or heterocyclic alkyl, such as, but not limited to, methyl, isopropyl, morpholino, pyrrolidino and 2,2,6,6-tetramethylpyrrolidino;

wherein $R_{12}$ is a phosphate protecting group such as, but not limited to, trichloroethyl, allyl, cyanoethyl and sulfonylethyl.

In another embodiment the present invention provides fluorescent structural analogs of the commonly occurring and analog nucleosides and their derivatives. The compounds of these structures, F, G, H, I and J, contain a triphosphate group (TPO), $R_2$, $R_3$ and $R_4$ derivatizing groups and $R_7$ and $R_{13}$, which can be hydrogen or hydroxyl groups.

Structure F

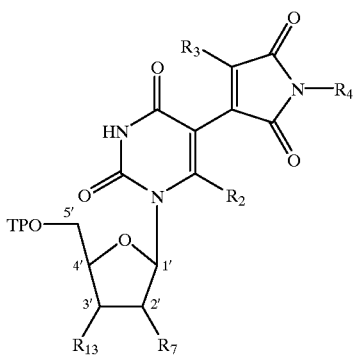

Structure G

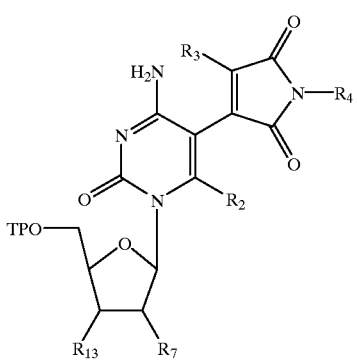

Structure H

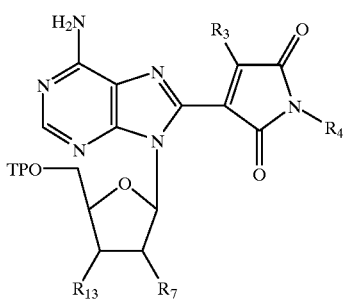

Structure I

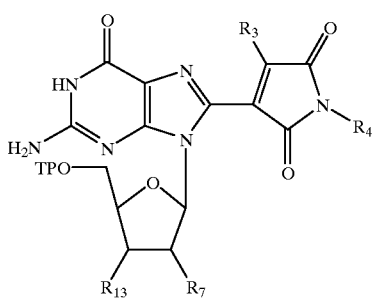

Structure J

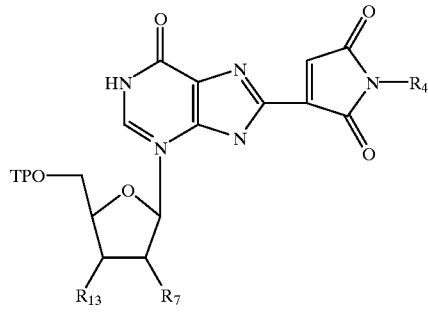

wherein $R_2$ and $R_3$ can be hydrogen, methyl, halogen, or an unsaturated moiety having a formula:

$(CH=CH)_m CH_2 Z;$ wherein m is an integer in a range of 1 to 6;

wherein Z can be hydrogen, hydroxyl, amine, amide, nitro, an electron withdrawing group, an electron attracting groups or an aromatic group;

wherein $R_4$ can be an alkyl or aromatic group.

Further according to the present invention there are provided methods of preparing the above nucleobases and nucleoside analogs.

Thus, According to a first aspect, there is provided a method of synthesizing a compound of a general formula:

D—B—M wherein:

B is selected from the group consisting of 9 of naturally occurring nitrogenous bases having a C—H group at positions 5 or 8, and derivatives of nitrogenous base-analogs having a C—H group at positions 5 or 8;

D is at least one derivatizing group, including hydrogen; and

M is a maleimide derivative.

The method is effected by executing the following method steps, in which in a first step a derivatized base DB is contacted with mercuric acetate and in a second step the product is condensed with N-alkylmaleimide, as follows:

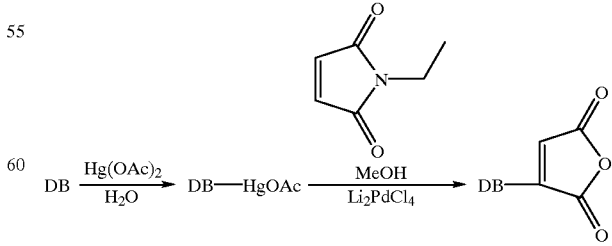

According to a second aspect, there is provided a method of synthesizing a compound of a structure selected from the group consisting of:

Structure Q

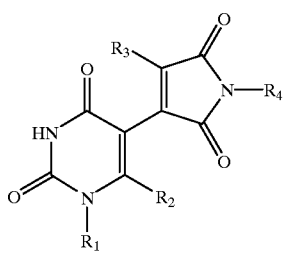

Structure R

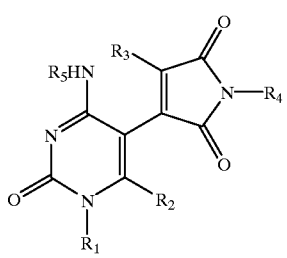

Structure S

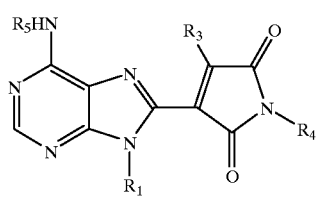

Structure T

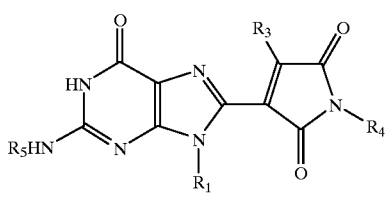

Structure U

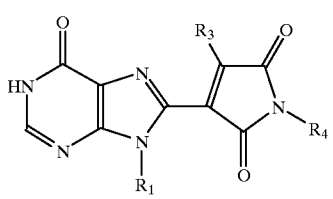

wherein:
R₁, R₂, R₃, R₄ and R₅ are each independently a derivatizing group, including hydrogen;
The method is effected by executing the following method steps, in which in a first step a derivatized base is contacted with mercuric acetate and in a second step the product is condensed with N-alkylmaleimide, as follows:

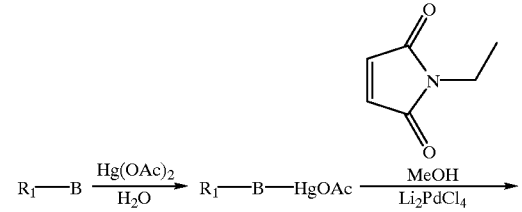

According to a third aspect, there is provided a method of synthesizing a compound of a structure selected from the structures consisting of:

Structure V

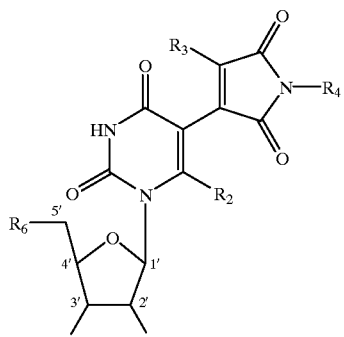

Structure W

Structure X

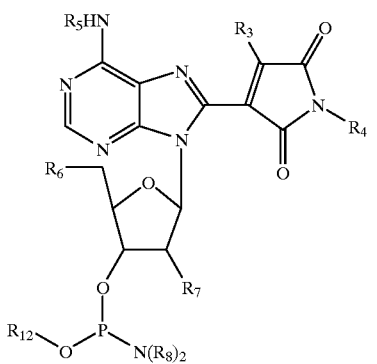

Structure Y

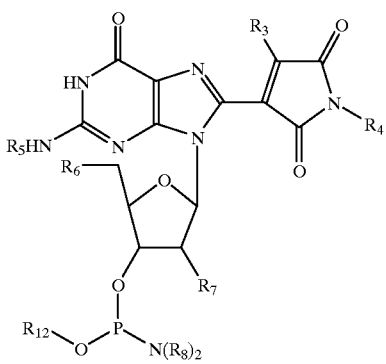

Structure Z

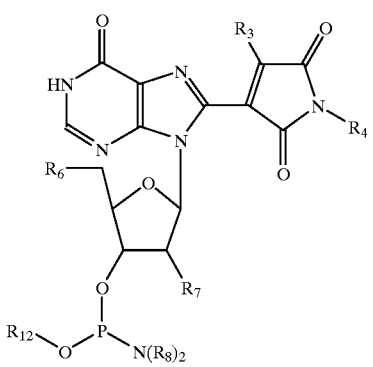

wherein $R_2$, $R_3$, $R_4$, $R_5$, $R_6$, $R_7$, $R_8$ and $R_{12}$, are each independently a derivatizing group;

The method is effected by executing the following method steps, in which in a first step a nucleoside is contacted with mercuric salt, followed condensation with N-alkylmaleimide. In a second step, amino groups of the nucleoside are protected with a protecting group (e.g., allyloxycarbamate). In a third step 5' hydroxyl of the nucleoside is protected with an acid labile group (e.g., dimethoxytrityl). Whereas in a final step, the product is condensed with allylic phosphoramidate reagent. All as follows:

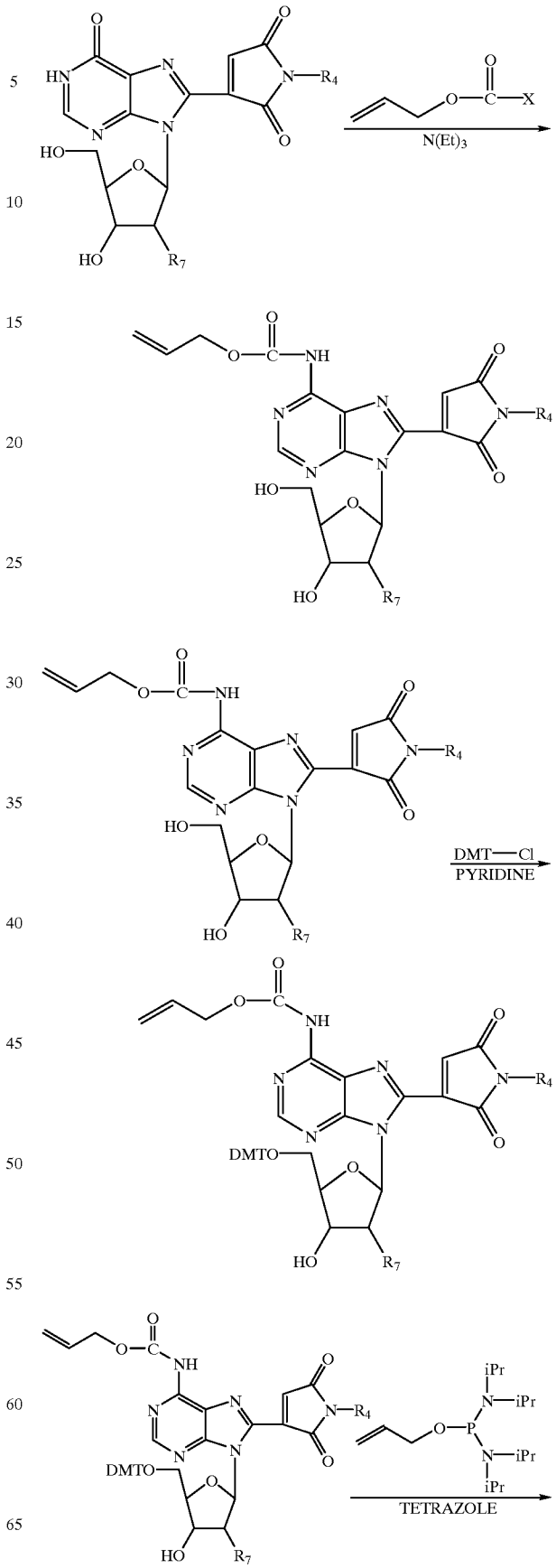

-continued

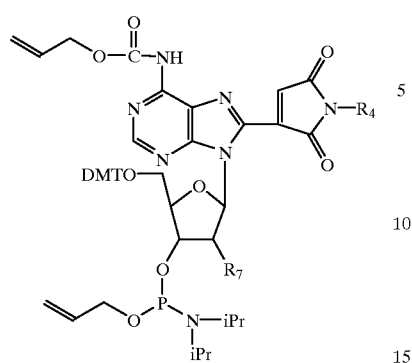

According to a fourth aspect, there is provided a method of synthesizing a compound of a structure selected from the group consisting of:

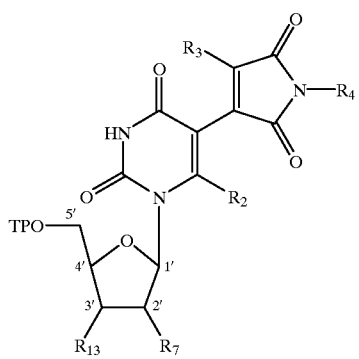

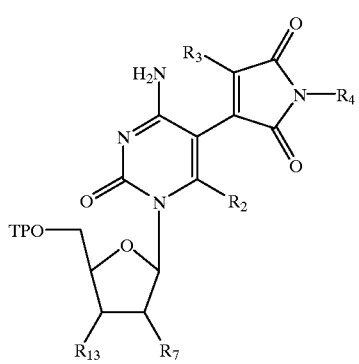

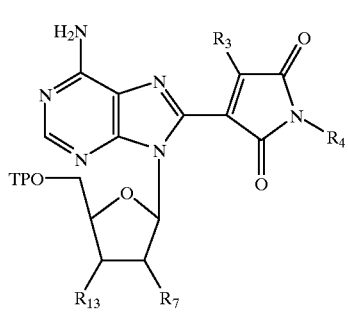

-continued

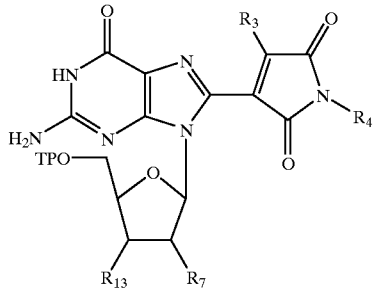

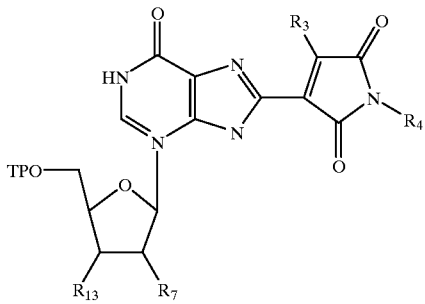

wherein TPO is a triphosphate group, $R_2$, $R_3$ and $R_4$ are each independently a derivatizing group, including hydrogen, and $R_7$ and $R_{13}$ are each independently selected from the group consisting of hydrogen and hydroxyl group;

The method is effected by executing the following method steps, in which in a first step a 5' triphosphate nucleoside is contacted with mercuric salt and in a second step the product is condensed with N-alkylmaleimide, as follows:

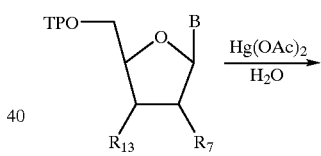

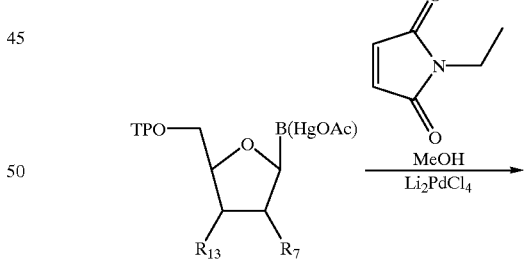

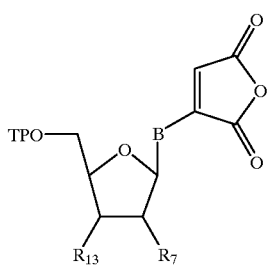

Further according to the present invention there are provided methods of using the above nucleoside structural analogs as follows.

According to one aspect, there is provided a method of hybridizing a target nucleic acid with a nucleic acid probe. Such a method can be used in liquid as well as surface hybridization reactions.

Hybridization according to the present invention can be performed in liquid (e.g., while performing a PCR or sequencing reaction) or on a surface. A surface hybridization according to the present invention includes processes such as, but not limited to, in situ hybridization, filter hybridization and solid phase (e.g., particulates) hybridization. These processes are well known in the art and therefore are not further elaborated herein. Protocols and uses for such processes can be found in, for example, Sambrook, J., Fritsch, E. F., Maniatis, T. (1989) Molecular Cloning. A Laboratory Manual. Cold Spring Harbor Laboratory Press, New York.

The method is performed by executing the following method step in which a sample including the target nucleic acid is contacted with a nucleic acid probe under hybridization conditions. The nucleic acid probe includes at least one fluorescent derivative of a nucleobase which includes a maleimide derivative attached at a C5 or C8 position of the nucleobase, as further detailed hereinabove.

According to another aspect, there is provided a method of determining a sequence of target nucleic acid. The method is effected by executing the following method steps, in which, in a first step the target nucleic acid is provided in a single stranded form (i.e., if it is double stranded, it is denatured). In a second step of the method, the single stranded form of the target nucleic acid is contacted, under hybridization conditions, with a sequencing primer (i.e., a primer hybridizable 5' to the region of the target to be sequenced), such that a sequence dependent primer-target nucleic acid duplex is formed. In a third step, the duplex is contacted, under polymerization conditions, with deoxynucleoside-tri-phosphates (four types), with at least one dideoxynucleoside-tri-phosphate and with a DNA polymerase. Further according to the method, at least one of the sequencing primer, deoxynucleoside-tri-phosphates or the dideoxynucleoside-tri-phosphate includes a fluorescent derivative of a nucleobase which includes a maleimide derivative attached at a C5 or C8 position of the nucleobase. If the sequencing primer or one or more of the includes the deoxynucleoside-tri-phosphates, then, four independent reactions are individually performed each with a different dideoxynucleoside-tri-phosphate, wherein reading the sequence following electrophoresis is dependent upon migration/lane. If, on the other hand, the different dideoxynucleoside-tri-phosphates are labeled with four distinctive fluorescent moieties, at least one is a fluorescent derivative of a nucleobase which includes a maleimide derivative attached at a C5 or C8 position of the nucleobase, then the different reactions can be performed in a single reaction tube, wherein reading the sequence following electrophoresis is based on migration/spectra.

According to another aspect, there is provided a method of synthesizing a polynucleotide. The method is effected by executing the following method step, in which, a solid phase synthesis protocol is used to sequentially, following a predetermined order, add nucleoside derivatives present initially in their phosphoramidite form to a growing chain of the polynucleotide in a 3' to 5' direction, wherein at least one of the nucleoside derivatives includes a fluorescent derivative of a nucleobase, the fluorescent derivative includes a maleimide derivative attached at a C5 or C8 position of the nucleobase.

According to another aspect, there is provided a method of synthesizing a polynucleotide. The method is effected by executing the following method steps, in which, in a first step, the template nucleic acid is provided in a single stranded form. In a second step of the method, the single stranded form of the template nucleic acid is contacted under hybridization conditions with at least one primer, such that a sequence dependent primer-target nucleic acid duplex is formed. In a third step of the method, the duplex is contacted under polymerization conditions with deoxynucleoside-tri-phosphates and with a DNA polymerase, wherein at least one of the primers or the deoxynucleoside-tri-phosphates includes a fluorescent derivative of a nucleobase, the fluorescent derivative includes a maleimide derivative attached at a C5 or C8 position of the nucleobase.

According to another aspect, there is provided a method of target dependent chemical ligation of probes. The method is effected by executing the following method steps, in which, in a first step, a first probe including a fluorescence moiety including a protected moiety being bound to the fluorescence moiety is provided. In a second step of the method, a second probe including a nucleophile moiety, the nucleophile moiety is selected such that when in appropriate proximity and orientation with respect to the protected moiety, the nucleophile moiety is allowed to react with the fluorescent moiety by addition reaction and consequently quench the fluorescence and release the protected moiety to yield a new fluorescent moiety fluorescing or chemiluminescing differently than the first fluorescence moiety. The first and second probes are selected such that by hybridizing to the target the appropriate proximity and orientation are obtained.

Thus, according to this embodiment, the present invention uses the novel fluorescent compounds as a key part in chemical amplification technology. This embodiment comprises a method of preparing fluorescent derivatives of uridine, cytidine, adenine and guanine, which are chemically attached to an oligonucleotide probe to form a fluorescent moiety which includes a protected moiety, which is bound to the fluorescence moiety. This moiety is not fluorescent, but upon reacting with a nucleophile, the fluorescence of the first fluorescence moiety is quenched and hydrolysis of the first fluorescence moiety takes place. The protected moiety is thus released to yield a new and different fluorescence or a chemiluminescence in different wavelength than the first moiety, as follows:

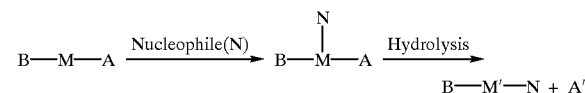

wherein B is a base from naturally occurring nucleotides and M-is a chemical moiety, such as maleimide and its derivatives, which upon conjugation with B forms a first fluorescent moiety (B—M). A is another chemical moiety which is fluorescent by itself, but when it is bound to M as (M—A), becomes a non-fluorescent moiety. Upon nucleophilic addition reaction between a nucleophile N and M, M becomes M', which facilitates hydrolysis of M and subsequently releases A as A' wherein A' is a new fluorescent moiety.

Figure 4:
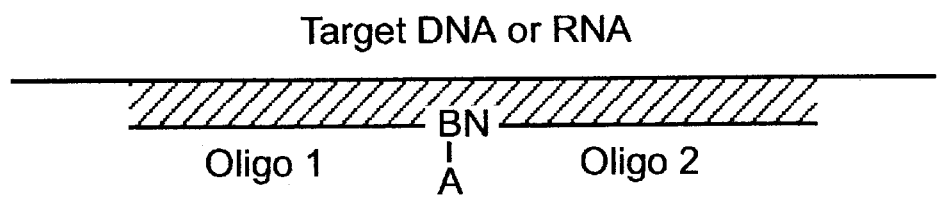
FIG. 4 is a schematic depiction of a chemical amplification reaction according to the present invention.

This embodiment of the present invention is thus useful, for example, in monitoring non-enzymatic (i.e., chemical) amplification reactions, such as the reactions disclosed in PCT/US94/06690 and in U.S. patent application No. 08/431, 527, both are incorporated by reference as if fully set forth herein, wherein the nucleophile is, for example, attached to an end of a second and juxtaposed oligonucleotide, as is shown in FIG. 4.

An example of structures operative according to this embodiment are described in Example 11 hereinunder.

Additional formula, advantages, methods of use and novel features of the invention will be set forth in the description which follows, and in part become apparent to those skilled in the art after examination of the following, or may be learned by practice of the invention.

Thus, disclosed herein and claimed are novel fluorescent nucleobases and nucleosides and methods of use of the fluorescent nucleosides in, for example, nucleic acid probes, for labeling proteins, hormones, steroids etc.

The novel fluorescent nucleoside analogs dyes of the present invention are derivatives of uracyl, cytidine and other pyrimidine derivatives at their C5-position, and of adenine and guanine and other purine derivatives at their 8-position.

Derivatization at these sites according to the present invention is to form a conjugation of extended double-bonds which results in forming novel fluorescent moieties.

One preferred embodiment is the use of these inherently fluorescent nucleoside analogs in the chemical and enzymatic synthesis of DNA hybridization probes including solid phase synthesis, template directed enzymatic polymerization and amplification, for use in various hybridization based reactions as fluorescent nucleic acid probes.

The fluorescent nucleic acid probes according to the present invention are capable of specific Watson-Crick base pairing with prescribed sequences of target DNA or RNA. This methodology is distinct from other non-radioactive methods of target DNA or RNA detection in that, the fluorescent nucleotide analogs serves as a part of the oligonucleotide hybridization probes and as fluorescent labels.

Another embodiment of the present invention relates to the use of the novel fluorescent nucleoside analogs in DNA sequencing.

EXAMPLES

Reference is now made to the following examples, which together with the above descriptions, illustrate the invention in a non limiting fashion.

Example 1

Preparation of 2'-Deoxy-5-N-ethylmaleimidouridine

A solution of 2'-deoxyuridine (2.28 grams, 10 mmol) and mercuric acetate (3.19 grams, 10 mmol) in 15 ml of water was heated with stirring at 60° C. for 5 hours. After removal of acetic acid formed in the reaction and water in vacuo, the white residue was suspended with N-ethylmaleimide (3.76 grams, 30 mmol) and 110 ml of 0.1 M lithium tetrachloropalladate in methanol at 60° C. for 12 hours. The mixture was cooled to room temperature, and a solution of hydrogen sulfide (850 mg, 25 mmol) in methanol (100 ml) was added with stirring, and filtered through Celite, and the solution was evaporated to dryness. The yellowish fluorescent solid residue was dissolved in methanol (100 ml) and suspended with 40 grams of silica gel, grade 9385, 230–40 Mesh, 60 A (Merck), and evaporated to dryness.

The coated silica was added on the top of a silica column (5×60 cm) using a solution of 10% methanol in dichloromethane as eluent and the resulting appropriate residue was evaporated to dryness. Rf: 0.41.

Yield: 947 mg. (27%).

mass spectrum m/e: 352 (molecular ion), 236 (uracyl-N-ethylmaleimide), 197, 179, 152, 126, 117 (deoxyribose).

$^1$H NMR [CDCl$_3$+CD$_3$OD] 9.21 (s, 1H, vinylmaleimide), 7.35 (s, 1H, C-6), 6.28 (t, 1H, J=7 Hz, C-1'), 4.45 (m, 1H, C-3'), 4.05 (m, 1H, C-4') 3.81 (m, 2H, C-5'), 3.42 ( q, 2H, J=13 Hz, N—CH2—,), 2.5, 2.2 (m, 2H, C-2'), 1.21 (t, 3H, J=13 Hz, CH3).

U.V. in methanol-max–285 nm.

Fluorescence-Excitation 360 nm, Emission 500 nm (See FIG. 1).

The following equation summarizes the above described reaction.

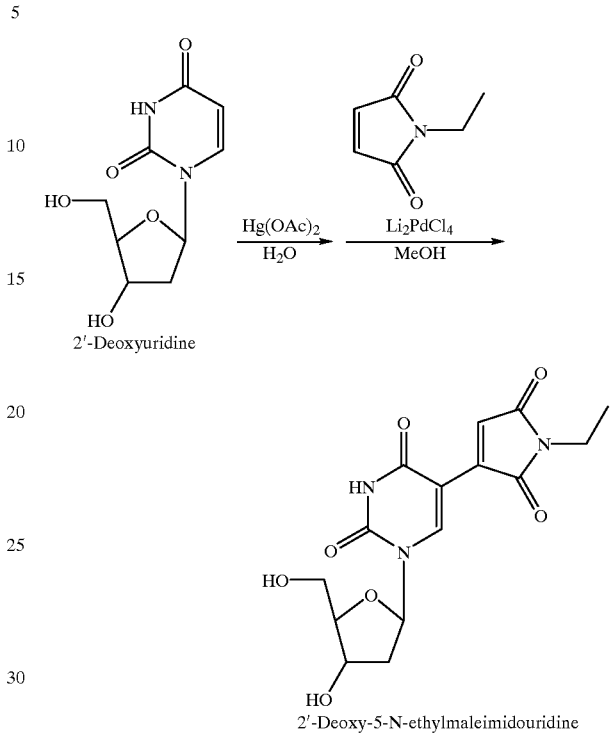

Example 2

Preparation of 5'-Dimethoxytrityl, 2'-deoxy, 5-N-ethylmaleimidouridine

To a cooled (0° C.) solution of 2'-Deoxy-5-N-ethylmaleimidouridine (3.51 gm, 10 mmol) in 50 ml of dry pyridine with stirring, was added dropwise a solution of dimethoxytritylchloride (3.72 gm, 11 mmol) in 50 ml pyridine. After the addition, the reaction was left to warn gradually to room temperature, and stirring was continued for 12 hours. The pyridine was evaporated in vacuo and the resulting brown oil was dissolved in ethyl acetate (200 ml) and washed with water (2×200 ml), followed by washing with a saturated aqueous sodium chloride solution, and the organic phase was dried with anhydrous sodium sulfate. The solvent was removed under vacuo and the crude brown oil was purified on silica gel column (4×80 cm) with 5%-methanol/0.5% pyridine in dichloromethane as eluent. The appropriate fraction was collected and evaporated to dryness.

Rf: 0.54.

$^1$H-NMR-[CDCl3] 9.00 (s, 1H, vinylmaleimide), 7.20–7.43 (m,13H, aromatic protons of DMTr), 6.79 (d, 4H, J=9 Hz, protons ortho to OCH3 of DMTr), 6.31 (t, 1H, J=7 Hz, C-1'), 4.35 (m, 1H, C-3'), 4.07 (m, 1H, C-4'), 3.75 (s, 6H, 2OCH3), 3.41–3.65 (m, 4H, C-5'+N—CH2), 2.26–2,52 (m, 2H, C-2'), 1.09 (t, 3H, J=13 Hz-CH3).

The following equation summarizes the above described reaction.

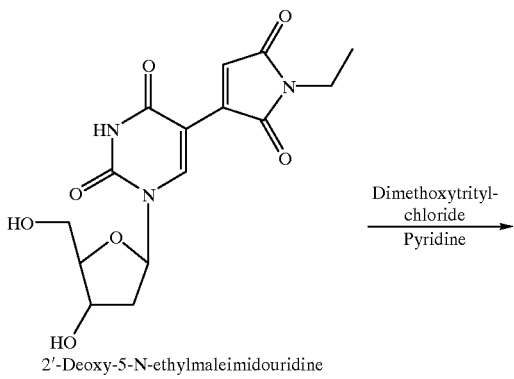

2'-Deoxy-5-N-ethylmaleimidouridine

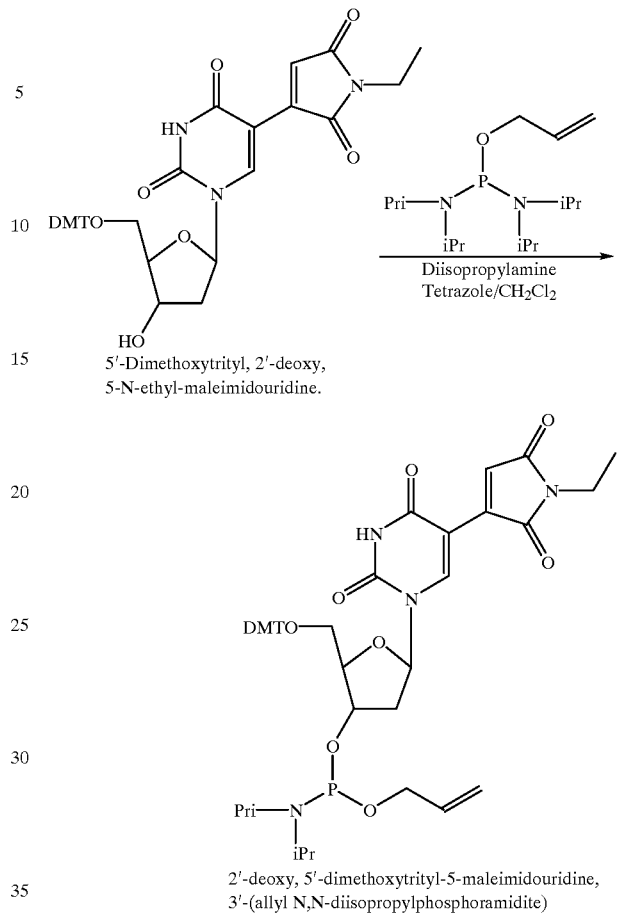

5'-Dimethoxytrityl, 2'-deoxy,
5-N-ethyl-maleimidouridine.

2'-deoxy, 5'-dimethoxytrityl-5-maleimidouridine,
3'-(allyl N,N-diisopropylphosphoramidite)

Example 3

Preparation of 2'-deoxy, 5'-dimethoxytrityluridine,
3'-(allyl N,N-diisopropylphosphoramidite)

The reagent (allyloxy)bis(diisopropylamino)phosphine, is prepared according to Hayakawa et al. in J. Am. Chem. Soc. (1990), 112:1691. To a solution of 5'-Dimethoxytrityl, 2'-deoxy, 5-N-ethylmaleimidouridine (6.03 gm, 9.25 mmol) in dichloromethane (60 ml), was added diisopropylamine (1.43 ml, 10.2 mmol), (allyloxy)bis(diisopropylamino) phosphine (4.3 ml, 14.0 mmol), and 1H-tetrazole (715 mg, 10.2 mmol). After 1.5 hours of stirring at 25° C., the mixture was poured into ethyl acetate (300 ml), washed with brine, and dried over $Na_2SO_4$. The resulting solution was concentrated to give a gummy material, which was dissolved in ethyl acetate (20 ml). The solution was added dropwise into hexane (800 ml) at −78° C. with stirring to give a powder, which was collected under vacuo through a paper filter (Watman #1) using a Buchner funnel. The resulting cake was dried under high vacuum to give a faint green powder which was collected and stored under Argon.

$^1$H NMR-[CDCl3] 9.02 (s, 1H, vinylic proton of the maleimide), 7.20–7.43 (m,14H, aromatic protons of DMTr and C-6), 6.76 (d, 4H, J=9 Hz, protons ortho to OCH3 of DMTr), 6.32 (s, 1H, C-1'), 5.91 (m, 1H, CH2—C$\underline{H}$=CH2), 4.97–5.49 (m, 2H, CH2—CH=C$\underline{H 2}$), 3.90–4.27 (m, 4H, C$\underline{H 2}$CH=CH2, C-3' and C-4'), 3.74 (s, 6H, 2OCH3), 3.40–3.56 (m, 6H, 2C$\underline{H}$(CH3)2, NCH2, and C-5'),2.10–2.70 (m, 2H, C-2'), 1.03–1.28 [m, 15H, 2CH(C$\underline{H 3}$)2 and CH3].

$^{31}$P NMR 149.61, 149.75

The following equation summarizes the above described reaction.

Example 4

Preparation of oligonucleotides by the allylic phosphoramidite method

The following CPG (controlled pore glass), was prepared according to Zhang et al. in Nucleic Acids Research (1997), 25:3080.

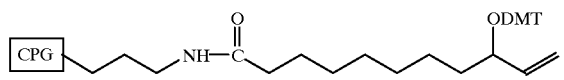

On this CPG, an oligonucleotide is synthesized, and deprotected as described therein.

The synthesis of allyl-and allyloxycarbonyl-protected 2'-deoxyribonucleoside 3'-phosphoramidites of cytidine, thymidine, guanine and adenine was done according to: Hayakawa et al. in J. Am. Chem. Soc. (1990), 112:1691.

The oligonucleotide that was synthesized using the method of the present invention has the following sequence:

5'-XCCACTACACCTACTATCCATTA-3'(SEQ ID NO:1)

Wherein X is (2'-deoxy, 5-maleimidouridine).

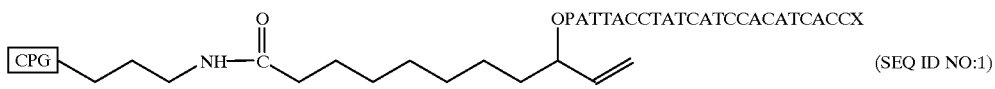

(SEQ ID NO:1)

Deprotection of the oligonucleotide from the CPG was accomplished by adding to the CPG a solution of the tris(dibenzylideneacetone)dipalladium(0)-chloroform complex (Aldrich) (140 mg, 0.135 mmol–2.5 equivalent/allyl), triphenylphosphine (360 mg, 1.37 mmol), and 1:1 equivalent of n-butylamine-formic acid in THF (6.7 ml, 8.04 mmol). The mixture was agitated at 50° C. for 4 hours. After being cooled to room temperature, the mixture was centrifuged, the supernatant fluid was decanted and the resulting CPG support was washed successively with THF (1 ml×20, acetone (1 ml×2). The product was then eluted from the support with (3×5 ml) portions of 0.1M triethylammonium acetate pH 6.5.

Figure 2:
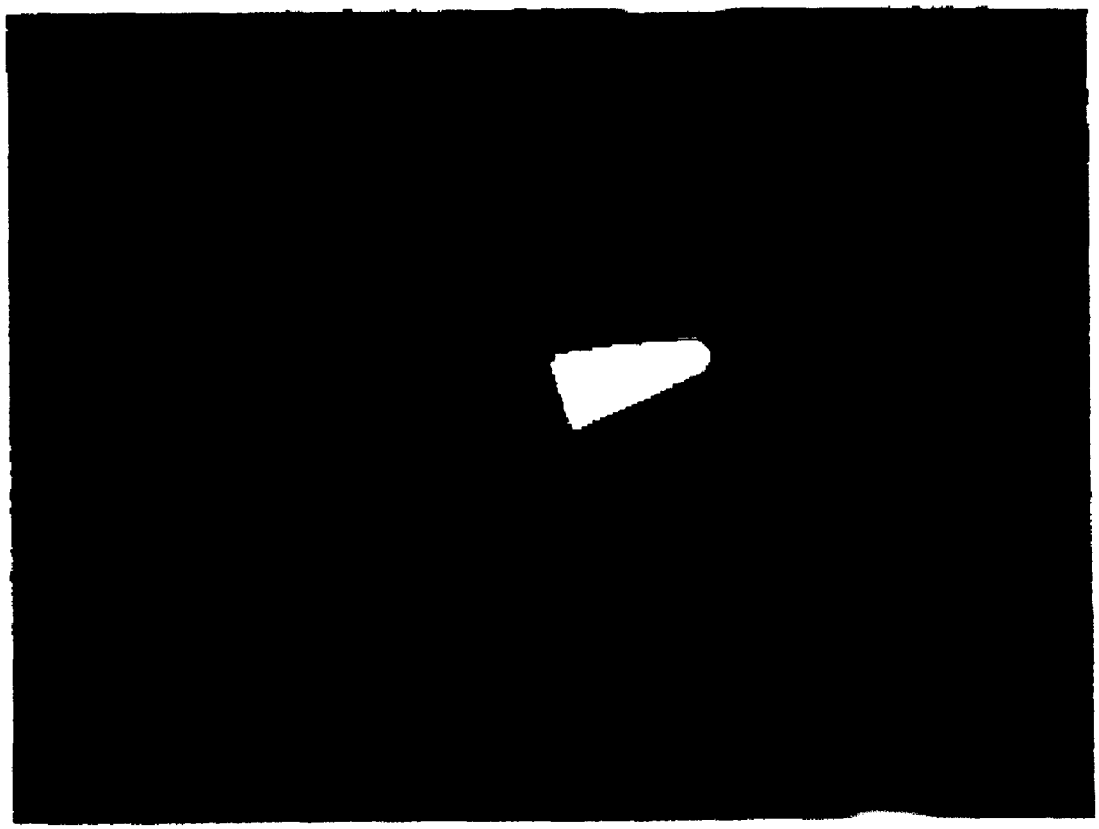
FIG. 2 is a photograph showing the fluorescence of a solution held in a tube containing an oligonucleotide in which a single structural analog according to the present invention is incorporated when irradiated at 360 nm using the GelDoc UV fluorescent gel documentation system by Bio-Rad Laboratories Inc.
Figure 3A:
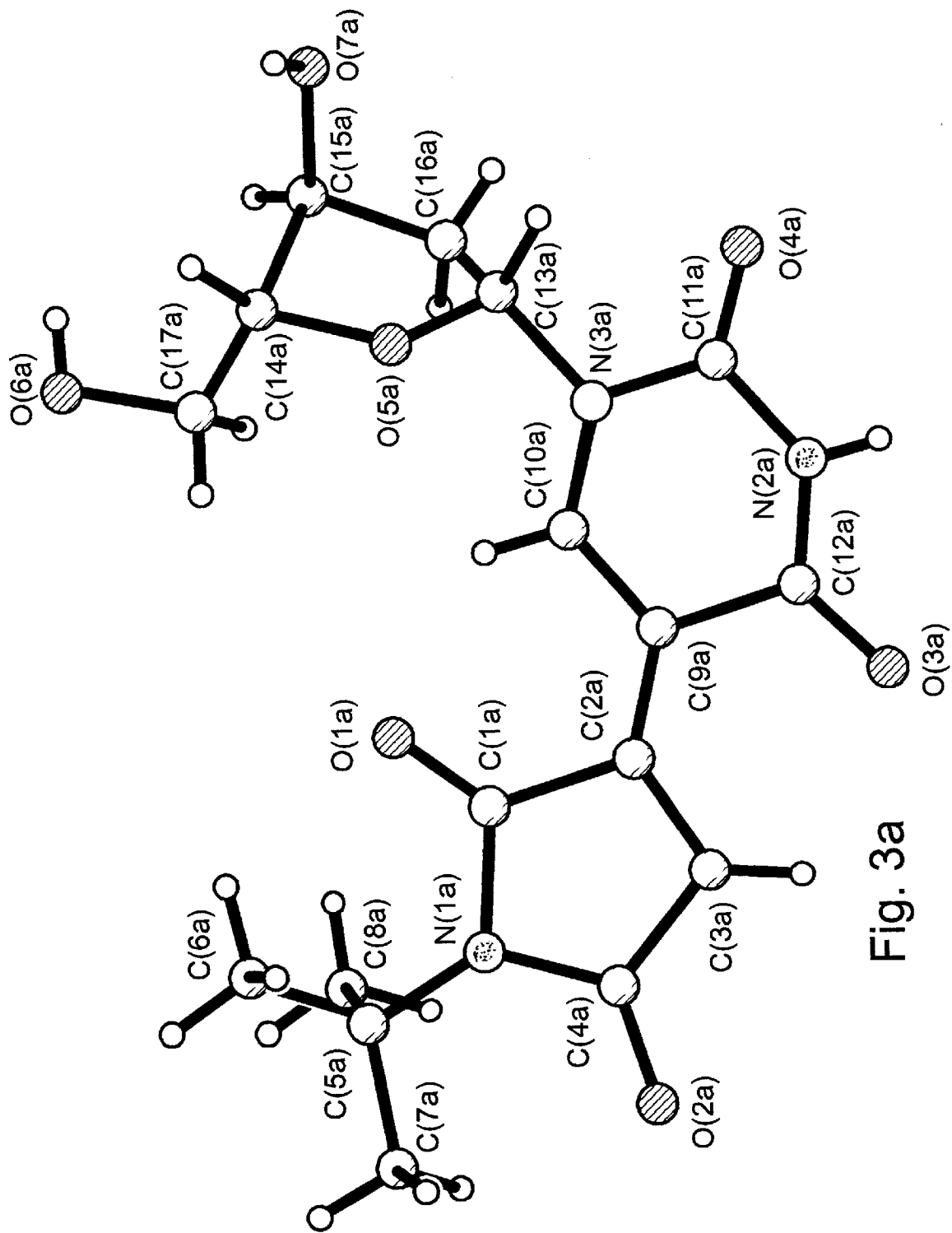
FIGS. 3a–d are X-ray diffraction derived three dimensional models of 2'-Deoxy-5-N-butylmaleimidouridine and lattice dimmers thereof according to the present invention.
Figure 3B:
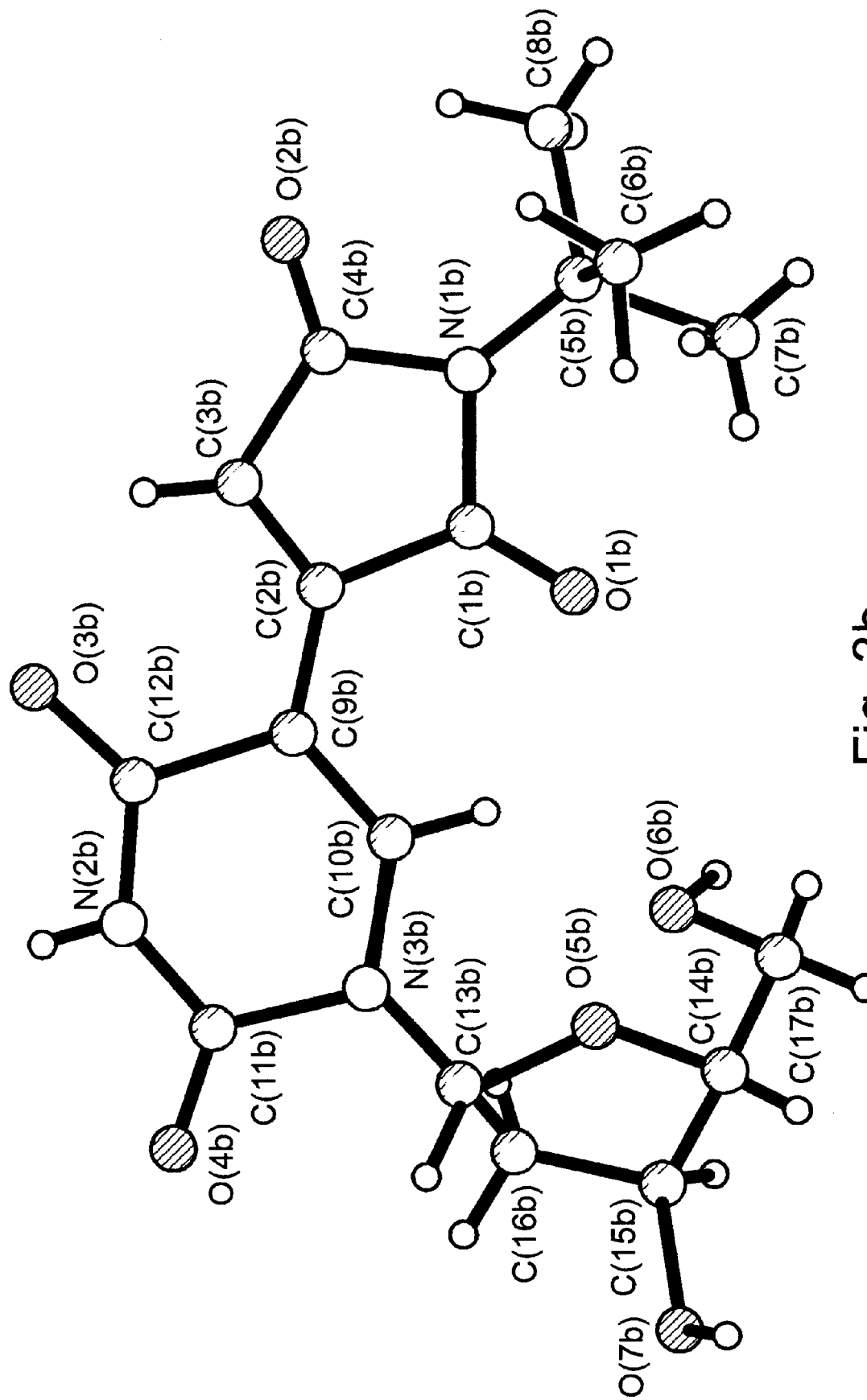
Figure 3C:
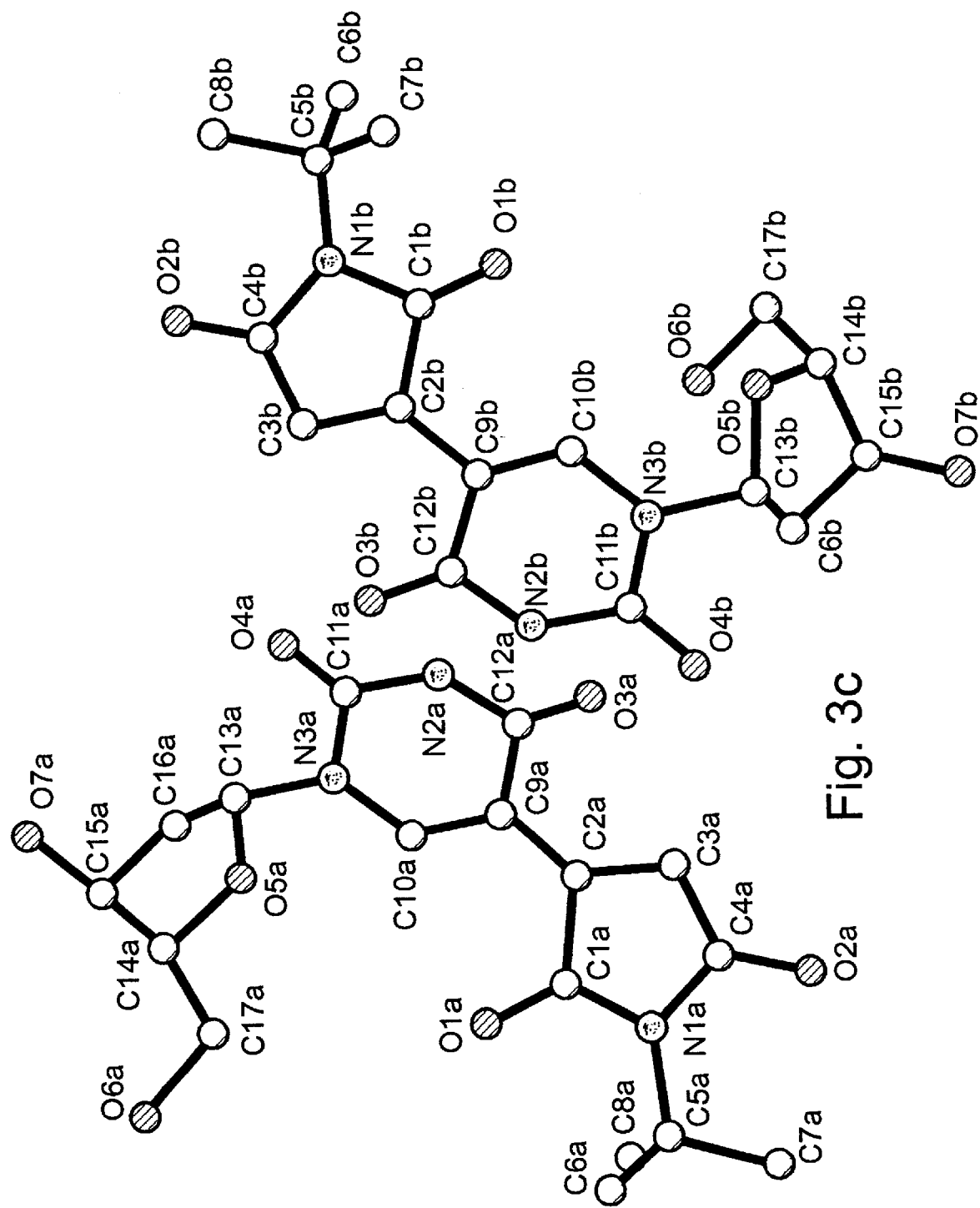
Figure 3D:
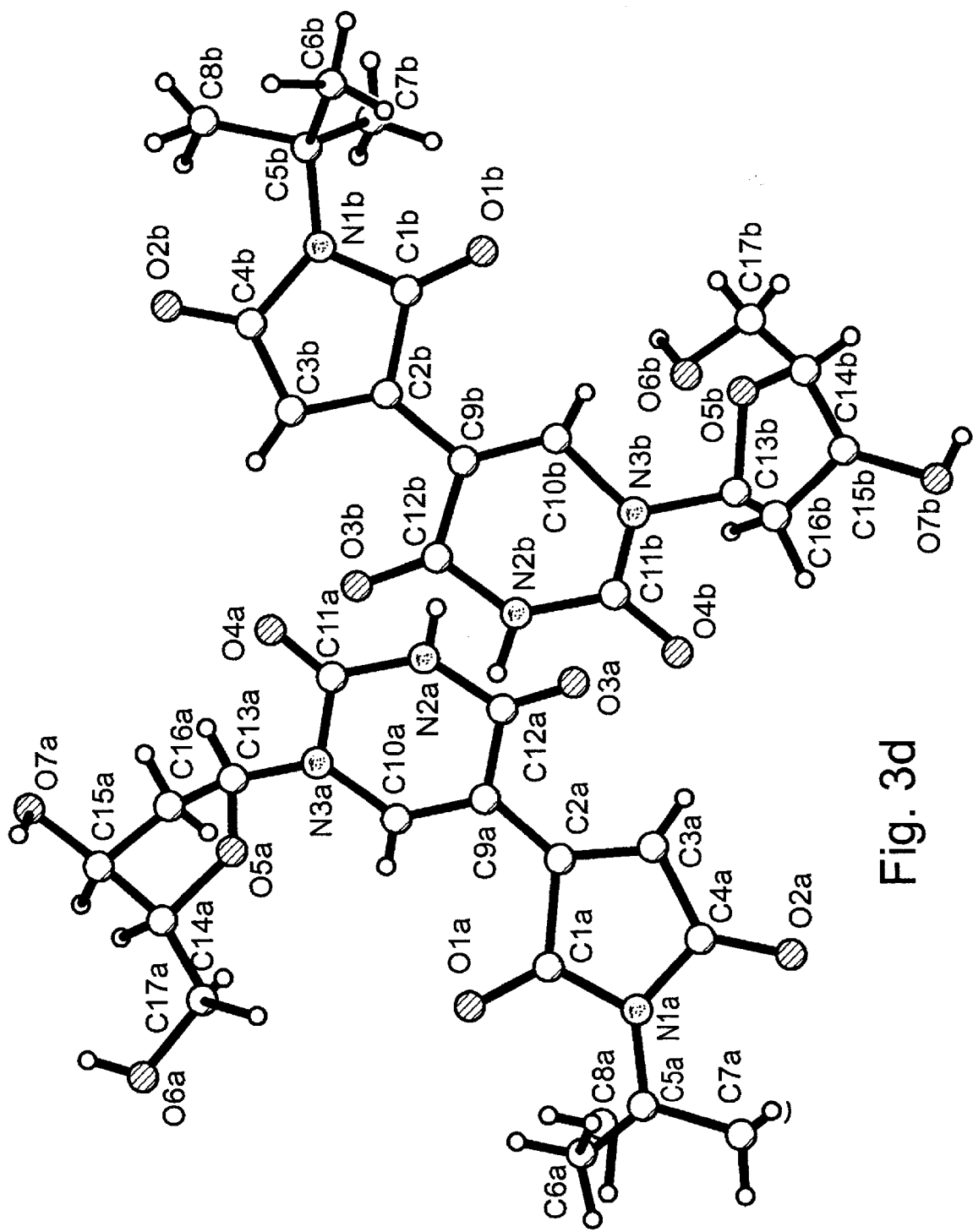

The supernatant was collected and concentrated by extraction with n-butanol. The volume of the water phase was reduced to 500 microliter. As shown in FIG. 2, this solution was highly fluorescent when irradiated at 360 nm.

Example 5

Preparation of 1-ethanol, 5-M-ethylmaleimidouracyl

To a solution of uracyl (10 grams, 89.2 mmol) in 100 dry dimethylformamide (DMF) was added ethylene carbonate (8.64 gm, 98.1 mmol) and sodium hydroxide (70 mg, 1.8 mmol). The solution was kept at 140° C. overnight with stirring. The solution was cooled to room temperature and the DMF was removed under reduced pressure.

TLC-in MeOH 30%-Dichloromethane 70% Rf-0.39

Yield-12.53 gram (90%).

The following equation summarizes the above described reaction.

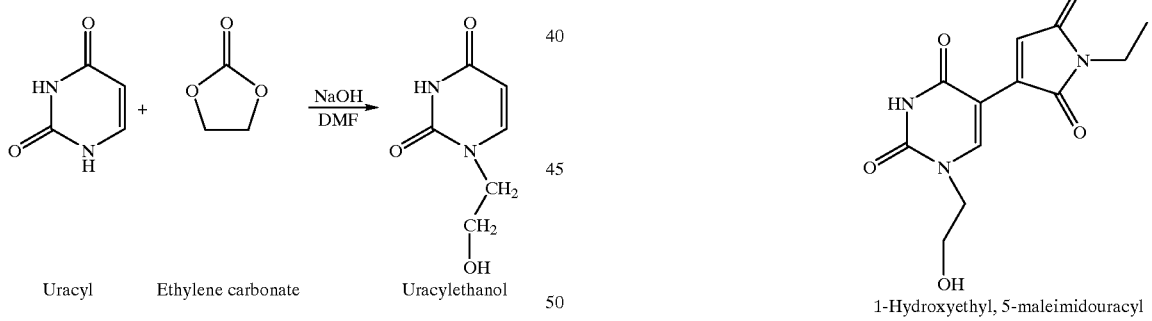

Example 6

Preparation of 1-Hydroxyethyl, 5-maleimidouracyl

To a solution of 1-uracylethanol (2.38 gm, 15.2 mmol) in 15 ml of water was added mercuric acetate (4.84 gm, 15.2 mmol). The reaction mixture was heated with stirring at 60° C. for 12 hours. After removal of acetic acid formed in the reaction and water in vacuo, the white residue was suspended with N-ethylmaleimide (5.0 gm, 39.9 mmol) and 150 ml of 0.1 M lithium tetrachloropalladate in methanol at 60° C. for 12 hours. The mixture was cooled to room temperature, and a solution of hydrogen sulfide (1.02 grams, 30 mmol) in methanol 100 ml was added with stirring, and filtered through Celite, and the solution was evaporated to dryness. The yellowish fluorescent solid residue was dissolved in methanol 100 ml and suspended with 40 gm of silica gel, grade 9385, 230–40 Mesh, 60 A (Merck), and evaporated to dryness.

The coated silica was added on the top of a silica column (5×60 cm) using a solution of 10% methanol in dichloromethane as eluent and the resulting fluorescent product was collected and the solvent was evaporated to dryness.

TLC-in 10% methanol in dichloromethane, Rf-0.45

$^1$H-NMR [CDCl3] 8.91 (s, 1H, vinylic proton of the maleimide), 7.18 (s, 1H, C-6), 3.65–3.88 (m, 4H, N-uracyl-C$\underline{H+b\ 2}$—C$\underline{H+b\ 2}$—OH), 3.54 and 3.98 (a-b quartet, 2H, N—C$\underline{H+b\ 2}$—CH3) of the maleimide), 1.14 (t, 3H, N—CH2—C$\underline{H+b\ 3}$)

The following equation summarizes the above described reaction.

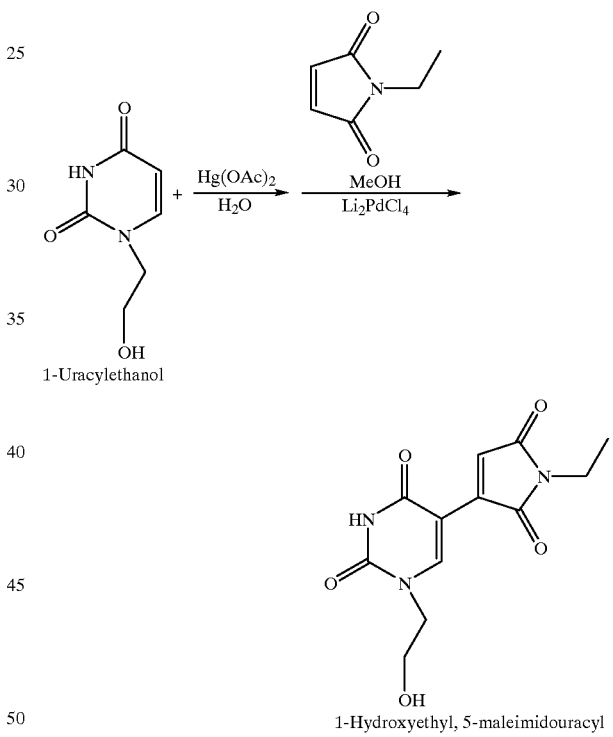

1-Hydroxyethyl, 5-maleimidouracyl

Example 7

Preparation of 1-(Hydroxyethylsuccinate), 5-N-ethylmaleimidouracyl

To a solution of 1-hydroxyethyl, 5-maleimidouracyl (0.28 gram, 1 mmol) and triethylamine (0.561 ml) in dry acetonitrile (20 ml), was added under Argon N,N'-disuccinimidylcarbonate (0.38 gram, 1.5 mmol) (Aldrich). The reaction mixture was stirred under Argon at room temperature for 4 hours. The solvent was removed under vacuum, and the solid was dissolved in ethyl acetate (50 ml) and washed with a solution of 5% sodium carbonate, followed by washing with brine and the organic phase was dried with anhydrous sodium sulfate. The ethyl acetate was reduced to a volume of 20 ml and the solution was added dropwise to stirred hexane. The solid which precipitated was collected under vacuum on a Watman paper #1, using a Buchner funnel. The powder was collected and stored under Argon. The product was fluorescent.

Yield: 0.48 gram (90%)

The following equation summarizes the above described reaction.

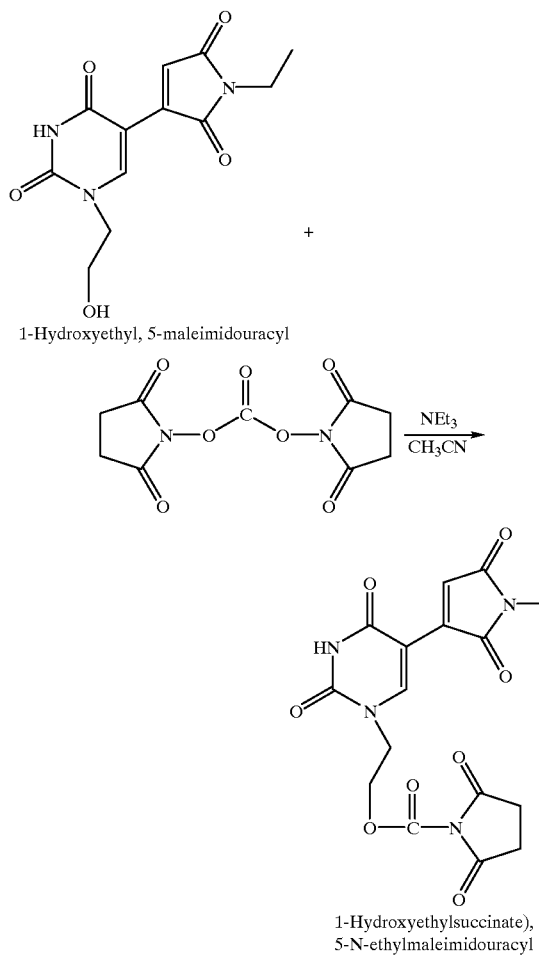

Example 8

Preparation of 2'-Deoxy-5-N-butylmaleimidouridine

A solution of 2'-deoxyuridine (2.28 grams, 10 mmol) and mercuric acetate (3.19 grams, 10 mmol) in 15 ml of water was heated with stirring at 60° C. for 5 hours. After removal of acetic acid formed in the reaction and water in vacuo, the white residue was suspended with N-t-butylmaleimide (3.76 grams, 24.5 mmol) and 110 ml of 0.1 M lithium tetrachloropalladate in methanol at 60° C. for 12 hours. The mixture was cooled to room temperature, and a solution of hydrogen sulfide (850 mg, 25 mmol) in methanol (100 ml) was added with stirring, and filtered through Celite, and the solution was evaporated to dryness. The yellowish fluorescent solid residue was dissolved in methanol (100 ml) and suspended with 40 grams of silica gel, grade 9385, 230–40 Mesh, 60 A (Merck), and evaporated to dryness.

The coated silica was added on the top of a silica column (5×60 cm) using a solution of 10% methanol in dichloromethane as eluent and the resulting appropriate residue was evaporated to dryness. Rf: 0.41.

Yield: 947 mg. (27%).

mass spectrum m/e: 380 (molecular ion), 236 (uracyl-N-butylmaleimide), 197, 179, 152, 126, 117 (deoxyribose).

$^1$H NMR [CDCl$_3$+CD$_3$OD] 9.21 (s, 1H, vinylmaleimide), 7.35 (s, 1H, C-6), 6.28 (t, 1H, J=7 Hz, C-1'), 4.45 (m, 1H, C-3'), 4.05 (m, 1H, C-4') 3.81 (m, 2H, C-5'), 3.42 (q, 2H, J=13 Hz, N—CH2—,), 2.5, 2.2 (m, 2H, C-2'), 1.21 (t, 3H, J=13 Hz, CH3).

U.V. in methanol-max-285 nm.

Fluorescence-Excitation 360 nm, Emission 500 nm.

The following equation summarizes the above described reaction.

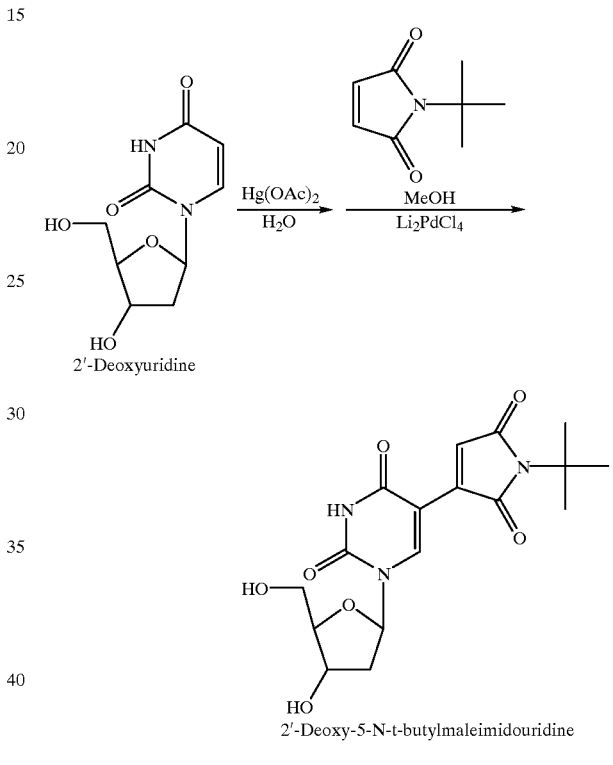

Example 9

Crystallizing 2'-Deoxy-5-N-butylmaleimidouridine and X-ray diffraction analysis thereof Data collection and treatment: Rigaku AFC5R four-circle diffractometer, MoKα, graphite monochromator (λ=0.71073 angstrom), 7962 reflections collected, 1.49°≦Θ≦27.50°, −7≦h≦7, 0≦k≦13, 0≦l≦35, ω scan method, scan width= 2.0°, scan speed 4°/min, typical half-height peak width= 0.85°, 3 standards collected 27 times each, with an 3% change in intensity, 4081 independent reflections (R-int= 0.0134).

Solution and refinement: Structure solved by Patterson method (SHELXS-93). Full-matrix least-squares refinement based on F$^2$ (SHELXL-93). Idealized hydrogens were placed and refined in a riding mode. 228 parameters with 19 restraints were employed Tables 1–3 below provide crystallography data. FIGS. 3a–d provide X-ray diffraction derived three dimensional models of 2'-Deoxy-5 -N-butylmaleimidouridine and lattice dimmers thereof according to the present invention.

TABLE 1

Crystal data and structure refinement

| | |
|---|---|
| Empirical formula: | $C_{34}H_{42}N_6O_{14}$ |
| Color | yellow |
| Type | needles |
| Formula weight: | 758.74 |
| Temperature: | 110° K. |
| Wavelength: | 0.71073 angstrom |
| Crystal system | monoclinic |
| Space group | P2(1) (No. 4) |
| Unit cell dimensions | a = 5.9980(10) angstrom; α = 90° |
| | b = 10.401(2) angstrom; β = 91.43 (3)° |
| | c = 27.403(5) angstrom; γ = 90° |
| Volume | 1709.0(5) angstrom$^3$ |
| Z | 2 |
| Density (calculated) | 1.474 Mg/m$^3$ |
| Absorption coefficient | 0.116 mm$^{-1}$ |
| F(000) | 800 |
| Crystal size | 0.05 × 0.05 × 0.03 mm$^3$ |
| Theta range for data collection | 1.49° to 27.50° |
| Index ranges | $-7 \leq h \leq 7, -13 \leq k \leq 2, -4 \leq 1 \leq 35$ |
| Reflections collected | 4239 |
| Independent reflections | 4081 [R(int) = 0.0134] |
| Refinement method | Full-matrix least-squares on F$^2$ |
| Data/restraints/parameters | 2558/19/228 |
| Goodness-of-fit on F$^2$ | 1.027 |
| Final R indices [I > 2Σ(I)] | R1 = 0.1609, wR2 = 0.4028 |
| R indices (all data) | R1 = 0.2480, wR2 = 0.5444 |
| Absolute structure parameter | 1 (7) |
| Largest diffraction peak and hole | 1.439 and −1.133 e·angstrom$^{-3}$ |
| Fw | 379.37 |
| Dc | 1.474 Mg/M$^3$ |
| μ | 0.116 mm-1 |

TABLE 2

Atomic coordinates (× 10$^4$) and equivalent isotropic displacement parameters (A$^2$ × 10$^3$). U(eq) is defined as one third of the trace of the orthogonalized Uij tensor.

| | X | y | z | U(eq) |
|---|---|---|---|---|
| 0(1A) | 3040(23) | 5754(16) | 888(5) | 36(3) |
| 0(2A) | 6256(21) | 9772(15) | 862(5) | 31(3) |
| 0(3A) | −617(22) | 9321(15) | 1907(5) | 29(3) |
| 0(4A) | −4957(21) | 5878(16) | 2343(4) | 32(3) |
| 0(5A) | −113(22) | 3451(15) | 1885(5) | 29(3) |
| 0(6A) | 361(21) | 1306(15) | 818(4) | 30(3) |
| 0(7A) | −3756(26) | 1404(19) | 2036(6) | 45(4) |
| N(1A) | 5309(22) | 7607(15) | 776(5) | 17(3) |
| N(2A) | −2706(25) | 7546(17) | 2106(5) | 23(3) |
| N(3A) | −1620(30) | 5437(21) | 1928(6) | 38(5) |
| C(1A) | 3529(25) | 6879(18) | 1011(5) | 18(4) |
| C(2A) | 2315(31) | 7714(22) | 1393(6) | 27(4) |
| C(3A) | 3311(29) | 8885(21) | 1366(6) | 26(4) |
| C(4A) | 5116(28) | 8815(20) | 997(6) | 21(4) |
| C(5A) | 6492(25) | 7173(18) | 339(6) | 16(4) |
| C(6A) | 7328(35) | 5819(25) | 463(8) | 38(5) |
| C(7A) | 8339(34) | 8097(24) | 248(8) | 35(5) |
| C(8A) | 4798(34) | 7128(24) | −82(7) | 32(4) |
| C(9A) | 518(27) | 7188(19) | 1639(6) | 18(4) |
| C(10A) | 145(31) | 5914(22) | 1698(7) | 24(4) |
| C(IIA) | −3252(31) | 6252(24) | 2148(5) | 33(5) |
| C(12A) | −1028(36) | 8114(24) | 1917(8) | 33(5) |
| C(13A) | −2011(28) | 4060(20) | 2007(6) | 22(4) |
| C(14A) | −495(29) | 2314(20) | 1562(6) | 23(4) |
| C(I5A) | −3235(29) | 2128(21) | 1620(6) | 25(4) |
| C(16A) | −3949(32) | 3495(22) | 1695(7) | 31(4) |
| C(17A) | 142(30) | 2444(20) | 1070(6) | 24(4) |
| O(3B) | −498(22) | 6058(15) | 3034(5) | 31(3) |
| O(4B) | 4678(23) | 9109(16) | 2668(5) | 36(3) |
| O(1B) | −3047(22) | 9545(15) | 4240(5) | 32(3) |
| O(2B) | −7197(24) | 5856(18) | 4112(5) | 42(4) |

TABLE 2-continued

Atomic coordinates (× 10$^4$) and equivalent isotropic displacement parameters (A$^2$ × 10$^3$). U(eq) is defined as one third of the trace of the orthogonalized Uij tensor.

| | X | y | z | U(eq) |
|---|---|---|---|---|
| O(5B) | 2138(24) | 11535(17) | 3673(5) | 39(4) |
| O(6B) | −2199(38) | 12235(28) | 3312(8) | 85(6) |
| O(7B) | 4169(27) | 13748(20) | 3020(6) | 52(4) |
| N(1B) | −5623(22) | 7812(16) | 4326(5) | 19(3) |
| N(2B) | 2067(28) | 7627(19) | 2873(6) | 32(4) |
| N(3B) | 1820(29) | 9668(21) | 3218(6) | 35(4) |
| C(IB) | −3752(29) | 8514(21) | 4098(6) | 28(4) |
| C(2B) | −2845(28) | 7750(20) | 3685(6) | 24(4) |
| C(3B) | −3977(29) | 6622(20) | 3645(6) | 23(4) |
| C(4B) | −5760(36) | 6637(26) | 4032(8) | 41(5) |
| C(5B) | −6607(32) | 8225(22) | 4770(7) | 30(5) |
| C(6B) | −4869(38) | 8232(27) | 5171(8) | 43(5) |
| C(7B) | −7609(37) | 9626(26) | 4690(8) | 40(5) |
| C(8B) | −8601(34) | 7302(25) | 4899(8) | 38(5) |
| C(9B) | −952(32) | 8081(22) | 3436(7) | 29(4) |
| C(10B) | −61(30) | 9309(21) | 3433(6) | 25(4) |
| C(11B) | 2989(30) | 8822(23) | 2900(6) | 34(5) |
| C(12B) | 186(33) | 7172(23) | 3092(7) | 32(5) |
| C(13B) | 2886(37) | 10998(26) | 3226(8) | 41(5) |
| C(I4B) | 1379(39) | 12833(29) | 3611(9) | 45(6) |
| C(15B) | 2036(33) | 13170(22) | 3083(7) | 29(4) |
| C(I6B) | 2178(32) | 11899(21) | 2846(7) | 30(4) |
| C(17B) | −873(54) | 12973(42) | 3688(13) | 76(9) |

TABLE 3

Bond lengths [angstrom] and angles [°]

| | |
|---|---|
| O(IA)-C(IA) | 1.25(3) |
| O(2A)-C(4A) | 1.27(2) |
| O(3A)-C(12A) | 1.28(3) |
| O(4A)-C(11A) | 1.23(2) |
| O(5A)-C(13A) | 1.35(3) |
| O(SA)-C(14A) | 1.49(2) |
| 0(6A)-C(17A) | 1.38(2) |
| 0(7A)-C(15A) | 1.41(3) |
| N(IA)-C(4A) | 1.40(3) |
| N(IA)-C(IA) | 1.47(2) |
| N(1A)-C(SA) | 1.48(2) |
| N(2A)-C(12A) | 1.29(3) |
| N(2A)-C(IIA) | 1.39(3) |
| N(3A)-C(IOA) | 1.34(3) |
| N(3A)-C(11A) | 1.44(3) |
| N(3A)-C(13A) | 1.47(3) |
| C(1A)-C(2A) | 1.55(3) |
| C(2A)-C(3A) | 1.36(3) |
| C(2A)-C(9A) | 1.40(3) |
| C(3A)-C(4A) | 1.50(2) |
| C(5A)-C(7A) | 1.49(3) |
| C(SA)-C(BA) | 1.52(2) |
| C(5A)-C(6A) | 1.53(3) |
| C(9A)-C(IOA) | 1.35(3) |
| C(9A)-C(I2A) | 1.55(3) |
| C(13A)-C(16A) | 1.54(3) |
| C(14A)-C(17A) | 1.42(2) |
| C(14A)-C(15A) | 1.67(2) |
| C(15A)-C(16A) | 1.50(3) |
| O(3B)-C(12B) | 1.24(3) |
| O(4B)-C(11B) | 1.25(2) |
| O(1B)-C(IB) | 1.21(3) |
| O(2B)-C(4B) | 1.21(3) |
| O(5B)-C(13B) | 1.43(3) |
| O(5B)-C(14B) | 1.43(3) |
| O(6B)-C(17B) | 1.50(4) |
| O(7B)-C(15B) | 1.43(3) |
| N(1B)-C(5B) | 1.43(2) |
| N(1B)-C(4B) | 1.47(3) |

TABLE 3-continued

| Bond lengths [angstrom] and angles [°] | |
|---|---|
| N(1B)-C(1B) | 1.49(3) |
| N(2B)-C(I2B) | 1.38(3) |
| N(2B)-C(IIB) | 1.36(3) |
| N(3B)-C(10B) | 1.34(3) |
| N(3B)-C(11B) | 1.43(3) |
| N(3B)-C(13B) | 1.52(3) |
| C(1B)-C(2B) | 1.49(3) |
| C(2B)-C(3B) | 1.36(3) |
| C(2B)-C(9B) | 1.38(3) |
| C(3B)-C(4B) | 1.52(3) |
| C(5B)-C(6B) | 1.50(3) |
| C(5B)-C(8B) | 1.58(3) |
| C(SB)-C(7B) | 1.59(3) |
| C(9B)-C(10B) | 1.38(3) |
| C(9B)-C(I2B) | 1.51(3) |
| C(13B)-C(16B) | 1.46(3) |
| C(14B)-C(17B) | 1.38(4) |
| C(14B)-C(15B) | 1.55(3) |
| C(I5B)-C(16B) | 1.48(3) |
| C(13A)-O(SA)-C(14A) | 113.6(14) |
| C(4A)-N(1A)-C(IA) | 101.7(12) |
| C(4A)-N(IA)-C(5A) | 132.1(14) |
| C(1A)-N(1A)-C(5A) | 124.5(14) |
| C(12A)-N(2A)-C(11A) | 132(2) |
| C(IOA)-N(3A)-C(11A) | 122(2) |
| C(10A)-N(3A)-C(I3A) | 124(2) |
| C(I1A)-N(3A)-C(13A) | 114(2) |
| O(1A)-C(1A)-N(1A) | 122(2) |
| O(1A)-C(1A)-C(2A) | 126(2) |
| N(1A)-C(IA)-C(2A) | 111(2) |
| C(3A)-C(2A)-C(9A) | 136(2) |
| C(3A)-C(2A)-C(1A) | 105(2) |
| C(9A)-C(2A)-C(IA) | 119(2) |
| C(2A)-C(3A)-C(4A) | 109(2) |
| O(2A)-C(4A)-N(1A) | 121.7(14) |
| (2A)-C(4A)-C(3A) | 124(2) |
| N(1A)-C(4A)-C(3A) | 114(2) |
| N(1A)-C(SA)-C(7A) | 108(2) |
| N(1A)-C(5A)-C(8A) | 107.4(13) |
| C(7A)-C(SA)-C(8A) | 112(2) |
| N(1A)-C(SA)-C(6A) | 105.3(14) |
| C(7A)-C(5A)-C(6A) | 113(2) |
| C(8A)-C(5A)-C(6A) | 110(2) |
| C(10A)-C(9A)-C(2A) | 125(2) |
| C(10A)-C(9A)-C(12A) | 117(2) |
| C(2A)-C(9A)-C(12A) | 118(2) |
| N(3A)-C(10A)-C(9A) | 124(2) |
| O(4A)-C(11A)-N(2A) | 123(2) |
| O(4A)-C(11A)-N(3A) | 125(2) |
| N(2A)-C(IIA)-N(3A) | 112(2) |
| N(2A)-C(I2A)-O(3A) | 128(2) |
| N(2A)-C(12A)-C(9A) | 113(2) |
| O(3A)-C(12A)-C(9A) | 119(2) |
| O(5A)-C(13A)-N(3A) | 106(2) |
| O(5A)-C(13A)-C(16A) | 108(2) |
| N(3A)-C(13A)-C(16A) | 114(2) |
| C(17A)-C(I4A)-0(5A) | 117(2) |
| C(17A)-C(14A)-C(15A) | 113(2) |
| O(SA)-C(14A)-C(15A) | 100.0(13) |
| O(7A)-C(ISA)-C(16A) | 109(2) |
| O(7A)-C(I5A)-C(14A) | 112(2) |
| C(16A)-C(15A)-C(14A) | 101(2) |
| C(I5A)-C(16A)-C(13A) | 103(2) |
| 0(6A)-C(17A)-C(14A) | 115(2) |
| C(13B)-O(SB)-C(14B) | 112(2) |
| C(SB)-N(1B)-C(4B) | 134(2) |
| C(5B)-N(1B)-C(1B) | 123(2) |
| C(4B)-N(1B)-C(IB) | 102.1(14) |
| C(12B)-N(2B)-C(11B) | 129(2) |
| C(IOB)-N(3B)-C(11B) | 122(2) |
| C(10B)-N(3B)-C(13B) | 127(2) |
| C(11B)-N(3B)-C(13B) | 111(2) |
| O(1B)-C(1B)-N(1B) | 124(2) |
| O(IB)-C(1B)-C(2B) | 126(2) |
| N(1B)-C(IB)-C(2B) | 110(2) |

TABLE 3-continued

| Bond lengths [angstrom] and angles [°] | |
|---|---|
| C(3B)-C(2B)-C(9B) | 126(2) |
| C(3B)-C(2B)-C(1B) | 109(2) |
| C(9B)-C(2B)-C(1B) | 124(2) |
| C(2B)-C(3B)-C(4B) | 107(2) |
| 0(2B)-C(4B)-N(1B) | 119(2) |
| 0(2B)-C(4B)-C(3B) | 129(2) |
| N(1B)-C(4B)-C(3B) | 111(2) |
| N(1B)-C(5B)-C(6B) | 109(2) |
| N(1B)-C(5B)-C(8B) | 110(2) |
| C(6B)-C(5B)-C(8B) | 111(2) |
| N(1B)-C(5B)-C(7B) | 109(2) |
| C(6B)-C(5B)-C(7B) | 111(2) |
| C(8B)-C(5B)-C(7B) | 108(2) |
| C(2B)-C(9B)-C(10B) | 124(2) |
| C(2B)-C(9B)-C(I2B) | 123(2) |
| C(10B)-C(9B)-C(12B) | 113(2) |
| N(3B)-C(10B)-C(9B) | 126(2) |
| O(4B)-C(11B)-N(2B) | 122(2) |
| O(4B)-C(I1B)-N(3B) | 125(2) |
| N(2B)-C(11B)-N(3B) | 113(2) |
| O(3B)-C(12B)-N(2B) | 123(2) |
| O(3B)-C(12B)-C(9B) | 121(2) |
| N(2B)-C(I2B)-C(9B) | 117(2) |
| O(5B)-C(13B)-C(16B) | 106(2) |
| O(5B)-C(13B)-N(3B) | 103(2) |
| C(163)-C(I3B)-N(3B) | 117(2) |
| C(17B)-C(14B)-O(5B) | 113(3) |
| C(I7B)-C(14B)-C(15B) | 113(2) |
| O(5B)-C(I4B)-C(I5B) | 104(2) |
| O(7B)-C(15B)-C(16B) | 105(2) |
| O(7B)-C(15B)-C(14B) | 117(2) |
| C(16B)-C(15B)-C(14B) | 103(2) |
| C(13B)-C(16B)-C(15B) | 106(2) |
| C(14B)-C(17B)-O(6B) | 110(3) |

Example 10

Production of the deoxy, dideoxy and phosphorylated forms of fluorescent nucleoside analogs Chemical syntheses are available in the literature for the derivatization as 2'-deoxy forms and 3'-deoxy forms of N-nucleoside, ethenonucleoside as well as of C-nucleosides, see, for example, Robins et al. (1973) *Can. J. Chem.* 51:1313; Jain et al. (1973) *J. Org. Chem.* 38:3719; DeClerq et al. (1987) *J. Med. Chem.* 30:481, which are incorporated by reference as if fully set forth herein.

Protocols for synthesis of 2'3'-dideoxy analogs are as reported by Lin et al. (1987) *J. Med. Chem.* 30:440 and Serafinowski, P. (1987) *Synthesis* 10:879, which is incorporated by reference as if fully set forth herein.

Enzymatic syntheses converts the monophosphate to the triphosphate analog with e.g., polynucleotide kinase using established procedures, as described by Schobert B. (1995) *Analytical Biochemistry* 226:288, which is incorporated by reference as if fully set forth herein.

In general, the 5'-monophosphates are prepared chemically by $POCL_2$ ad described in Lin and Brown (1989) *Nucl. Acids Res.* 17:10373; Yoshikawa et al. (1967) *Tetrahedron Lett.* 5095, which are incorporated by reference as if fully set forth herein. The corresponding triphosphates can be chemically synthesized according to the same authors or by Hoard and Ott (1965) *J. Am. Chem. Soc.* 87:1785, and Michelson (1964) *Biochim. Biophys. Acta.* 91:1.

That is, the monophosphates are treated with 1,1'-carbonildiimidazole followed with tributylammonium pyrophosphate in dimethylformamide under anhydrous conditions to give the triphosphorylated form.

Figure 5:
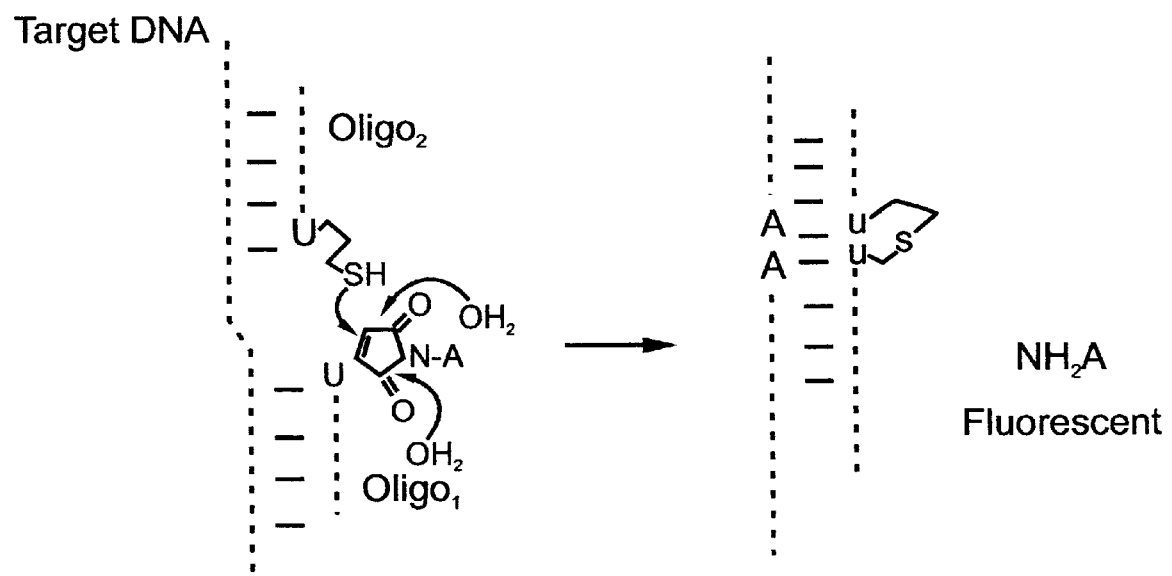
FIG. 5 is an example of structures operative while implementing a chemical amplification reaction as shown in FIG. 4 according to the present invention, wherein A is, for example, N-Acridinylmaleimide, as described by M. Machida et al. in Chem. Pharm. Bull. (1978), Vol 26, 596.

FIG. 5 provides an example of structures operative while implementing a chemical amplification reaction according to the present invention as specifically shown in FIG. 4.

A in FIG. 5, is for example, N-Acridinylmaleimide, as described by M. Machida et al. in Chem. Pharm. Bull. (1978), Vol 26, 596 as follows:

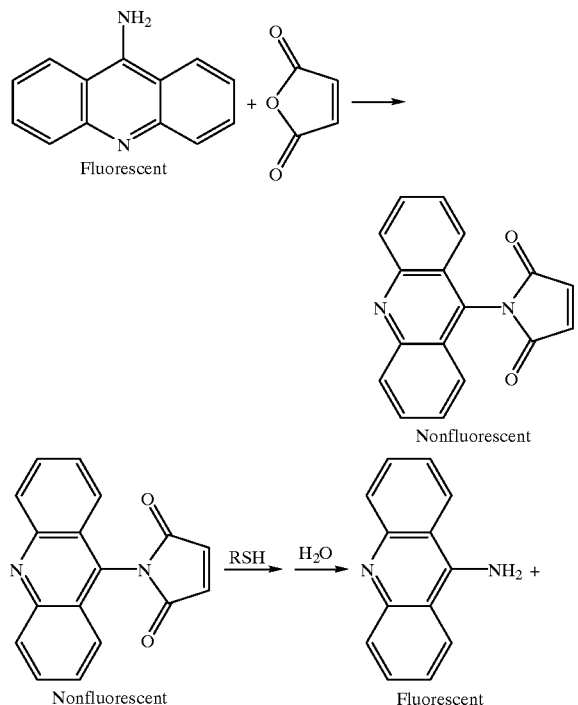

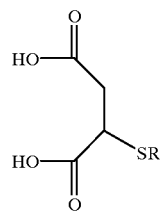

The above examples are described with specific emphasis on uridine derivatives. However, as will be appreciated by one ordinarily skilled in the art, and as was actually performed by the inventor of the present invention, very similar reactions can be devised for other pyrimidines and for purines to thereby obtain fluorescent structural homologs thereof.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A compound having a structure selected from the group consisting of:

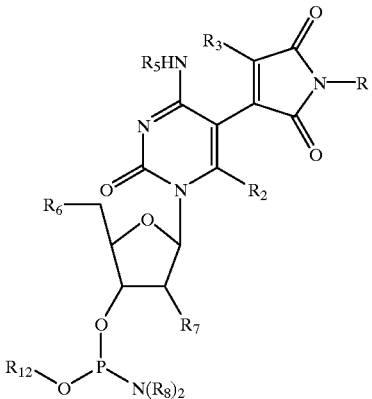

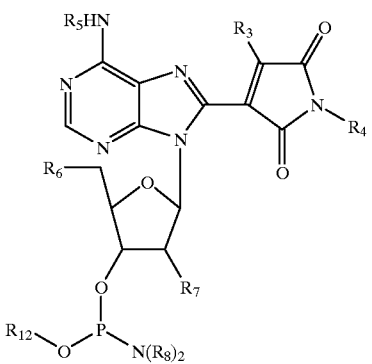

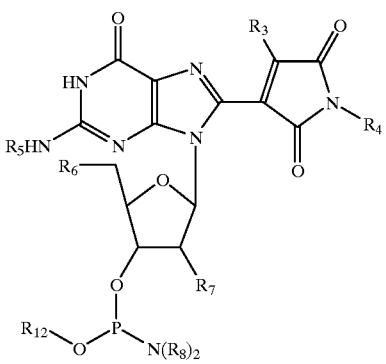

wherein:
$R_2$, $R_3$, $R_4$, $R_5$, $R_6$, $R_7$, $R_8$ and $R_{12}$, are each independently a derivatizing group.

2. The compound of claim 1, wherein $R_6$ is a chemical functionality group selected from the group consisting of hydroxylic group $OR_9$ and amino group $NR_{10}$, wherein $R_9$ is independently selected from the group consisting of an acid labile protecting group and a base labile protecting group, whereas $R_{10}$ is independently a nitrogen protecting group.

3. The compound of claim 2, wherein said acid labile protecting group is selected from the group consisting of triphenylmethyl, p-anisyldiphenylmethyl, di-p-anisyldiphenylmethyl, p-dimethoxy trityltrityl, formyl, t-butyloxycarbonyl, benzyloxycarbonyl, 2-chlorobenzyloxycarbonyl, 4-chlorobenzoyloxycarbonyl, 2,4-dichlorobenzyloxycarbonyl, furfurylcarbonyl, t-amyloxycarbonyl, adamantyloxycarbonyl, 2-phenylpropyl-(2)-oxycarbonyl, 2-(4-biphenyl)propyl-(2)-oxycarbonyl, 2-nitrophenylsulfenyl and diphenylphosphinyl.

4. The compound of claim 2, wherein said base labile protecting group is selected from the group consisting of trifluoroacetyl, 9-fluorenylmethyloxycarbonyl, allyloxycarbonyl, 4-toluenesulfonylethyloxycarbonyl, methylsulfonylethyloxycarbonyl, 2-cyano-t-butyloxycarbonyl, silyl ethers, and 2,2,2-trichloroethylcarbonate.

5. The compound of claim 2, wherein said nitrogen protecting group is selected from the group consisting of trifluoroacetyl, 9-fluorenylmethyloxycarbonyl, allyloxycarbonyl 4-toluenesulfonylethyloxycarbonyl, methylsulfonylethyloxycarbonyl, and 2-cyano-t-butyloxycarbonyl, chloroacetyl, acetoacetyl, and 2,2,2-trichloroethyloxycarbonyl.

6. The compound of claim 1, wherein $R_5$ is selected from the group consisting of an amino group $NR_{10}$, wherein $R_{10}$ is an acid labile protecting group, and a base labile protecting group.

7. The compound of claim 6, wherein said acid labile protecting group is selected from the group consisting of triphenylmethyl, p-anisyldiphenylmethyl, di-p-anisyldiphenylmethyl, p-dimethoxytrityl, formyl, t-butyloxycarbonyl, benzyloxycarbonyl, 2-chlorobenzyloxycarbonyl, 4-chlorobenzoyloxycarbonyl, 2,4-dichlorobenzyloxycarbonyl, furfurylcarbonyl, t-amyloxycarbonyl, adamantyloxycarbonyl, 2-phenylpropyl-(2)-oxycarbonyl, 2-(4-biphenyl)propyl-(2)-oxycarbonyl, di-p-anisyldiphenylmethyl, 2-nitrophenylsulfenyl and diphenylphosphinyl.

8. The compound of claim 6, wherein said base labile protecting group is selected from the group consisting of trifluoroacetyl, 9-fluorenylmethyloxycarbonyl, 4-toluenesulfonylethyloxycarbonyl, methylsulfonylethyloxycarbonyl and 2-cyano-t-butyloxycarbonyl.

9. The compound of claim 1, wherein $R_7$ is selected from the group consisting of hydrogen and $OR_{11}$, wherein $R_{11}$ is a chemical protecting group.

10. The compound of claim 9, wherein said $R_{11}$ protecting group is selected from the group consisting of lower aryl and alkylether.

11. The compound of claim 10, wherein said $R_{11}$ protecting group is selected from the group consisting of, triphenylmethyl, acetal, tetrahydropyranyl, silyl ether, trimethylsilyl and t-butyl-dimethylsilyl.

12. The compound of claim 10, wherein said $R_{11}$ protecting group is selected from the group consisting of hydroxylic and amino groups.

13. The compound of claim 1, wherein $R_8$ is selected from the group consisting of lower and heterocyclic alkyl.

14. The compound of claim 13, wherein $R_8$ is selected from the group consisting of methyl, isopropyl, morpholino, pyrrolidino and 2,2,6,6-tetramethylpyrrolidino.

15. The compound of claim 1, wherein $R_{12}$ is a phosphate protecting group.

16. The compound of claim 15, wherein said phosphate protecting group is selected from the group consisting of trichloroethyl, allyl, cyanoethyl and sulfonylethyl.

17. A compound selected from the group consisting of:

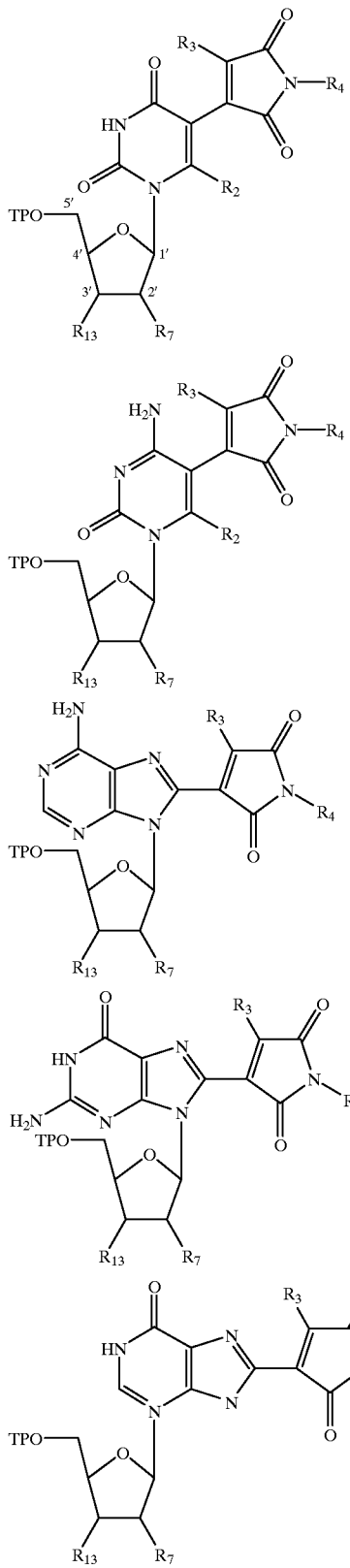

wherein TPO is a triphosphate group, $R_2$, $R_3$ and $R_4$ are each independently a derivatizing group, including hydrogen, and $R_7$ and $R_{13}$ are each independently selected from the group consisting of hydrogen and hydroxyl group.

18. The compound of claim 17, wherein:

$R_4$ is selected from the group consisting of alkyl and aromatic group.

19. A method of synthesizing a compound of a structure selected from the group consisting of:

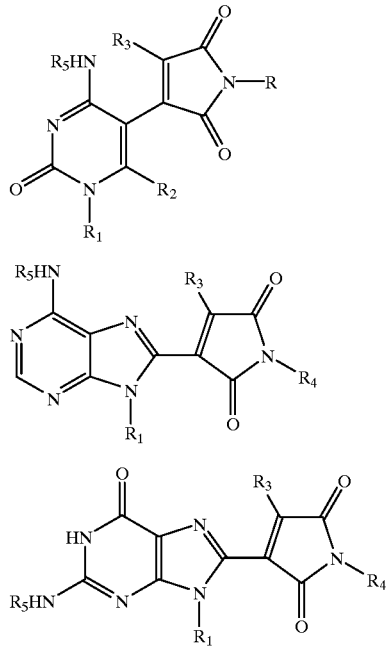

wherein:

$R_1$, $R_2$, $R_3$, $R_4$ and $R_5$ are each independently a derivatizing group, including hydrogen, the method comprising the steps of contacting a derivatized base with mercuric acetate and condensing with N-alkylmaleimide.

20. A method of synthesizing a compound of a structure selected from the group consisting of:

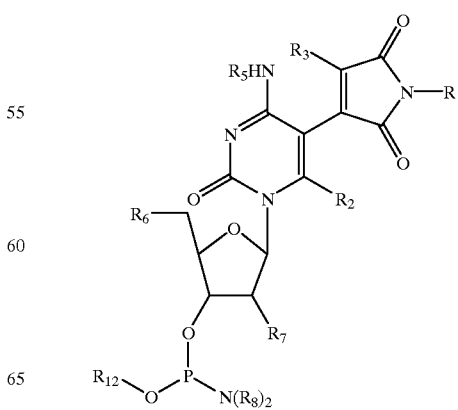

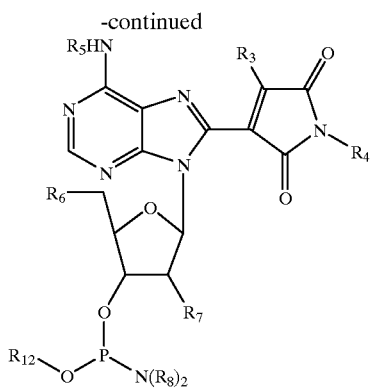

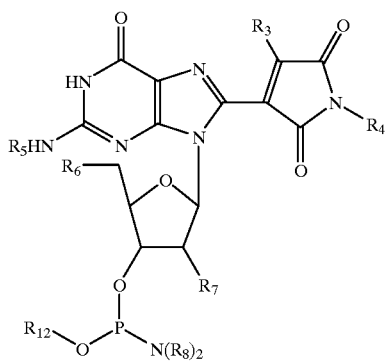

wherein $R_2$, $R_3$, $R_4$, $R_5$, $R_6$, $R_7$, $R_8$ and $R_{12}$, are each independently a derivatizing group, including hydrogen, the method comprising the steps of:

(a) contacting a nucleoside with mercuric salt, followed by condensation with N-alkylmaleimide;

(b) protecting amino groups of said nucleoside with a protecting group;

(c) protecting a 5' hydroxyl of said nucleoside with an acid labile group; and (d) condensing with allylic phosphoramidate reagent.

21. A method of synthesizing a compound of a structure selected from the group consisting of:

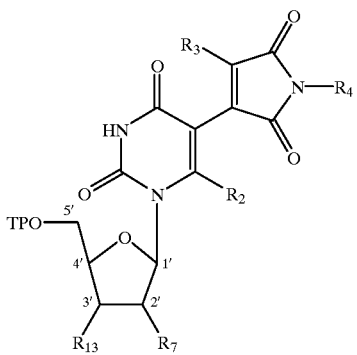

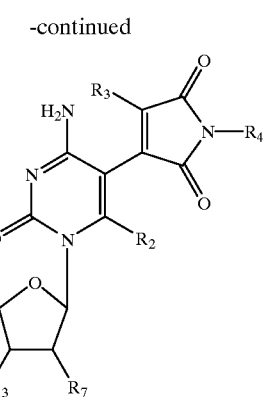

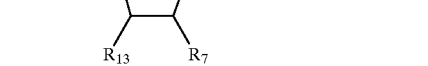

wherein TPO is a triphosphate group, $R_2$, $R_3$ and $R_4$ are each independently a derivatizing group, including hydrogen, and $R_7$ and $R_{13}$ are each independently selected from the group consisting of hydrogen and hydroxyl group; the method comprising the steps of contacting a 5' triphosphate nucleoside with mercuric salt and condensing with N-alkylmaleimide.

22. A compound having a structure selected from the group consisting of:

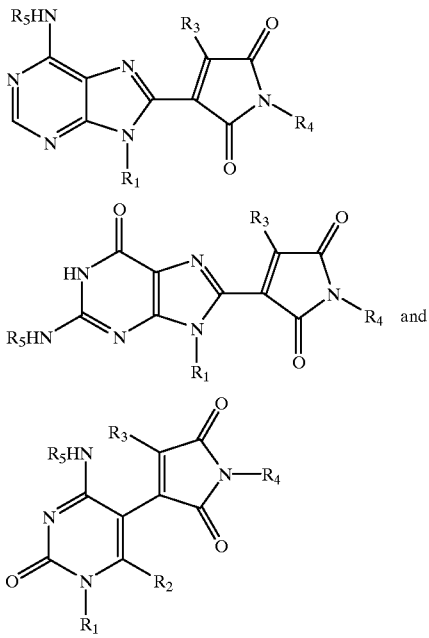

wherein:

$R_1$, $R_2$, $R_3$, $R_4$ and $R_5$ are each independently a derivatizing group, including hydrogen.

23. The compound of claim 22, wherein $R_5$ is selected from the group consisting of hydrogen and an amino protecting group useful in a protection of amino acids in peptide synthesis.

24. The compound of claim 23, wherein said amino protecting group is selected from the group consisting of trifluoroacetyl, acetyl, benzoyl, 9-fluorenylmethyloxycarbonyl, allyloxycarbonyl, 4-toluenesulfonylethyloxycarbonyl, methylsulfonylethyloxycarbonyl, 2-cyano-t-butyloxycarbonyl, chloroacetyl, acetoacetyl and 2,2,2-trichloroethyloxycarbonyl.

25. A compound having a structure:

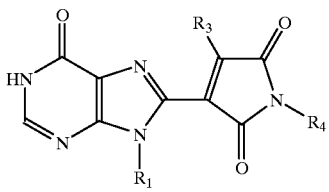

wherein:

$R_1$, $R_2$, $R_3$ and $R_4$ are each independently a derivatizing group, including hydrogen.

26. A compound having a structure selected from the group consisting of:

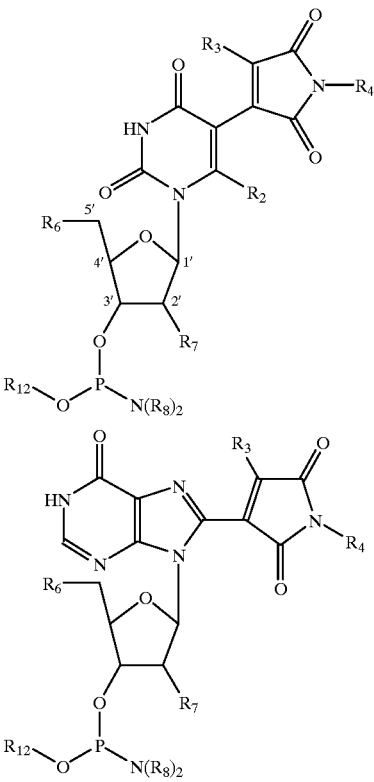

wherein:

$R_2$, $R_3$, $R_4$, $R_6$, $R_7$, $R_8$ and $R_{12}$, are each independently a derivatizing group.

27. The compound of claim 26, wherein $R_6$ is a chemical functionality group selected from the group consisting of hydroxylic group $OR_9$ and amino group $NR_{10}$, wherein $R_9$ is independently selected from the group consisting of an acid labile protecting group and a base labile protecting group, whereas $R_{10}$ is independently a nitrogen protecting group.

28. The compound of claim 27, wherein said base labile protecting group is selected from the group consisting of trifluoroacetyl, 9-fluorenylmethyloxycarbonyl, allyloxycarbonyl, 4-toluenesulfonylethyloxycarbonyl, methylsulfonylethyloxycarbonyl, 2-cyano-t-butyloxycarbonyl, silyl ethers, and 2,2,2-trichloroethylcarbonate.

29. The compound of claim 27, wherein said nitrogen protecting group is selected from the group consisting of trifluoroacetyl, 9-fluorenylmethyloxycarbonyl, allyloxycarbonyl 4-toluenesulfonylethyloxycarbonyl, methylsulfonylethyloxycarbonyl, and 2-cyano-t-butyloxycarbonyl, chloroacetyl, acetoacetyl, and 2,2,2-trichloroethyloxycarbonyl.

30. The compound of claim 27, wherein said acid labile protecting group is selected from the group consisting of triphenylmethyl, p-anisyldiphenylmethyl, di-p-anisyldiphenylmethyl, p-dimethoxy trityl, formyl, t-butyloxycarbonyl, benzyloxycarbonyl, 2-chlorobenzyloxycarbonyl, 4-chlorobenzoyloxycarbonyl, 2,4-dichlorobenzyloxycarbonyl, furfurylcarbonyl, t-amyloxycarbonyl, adamantyloxycarbonyl, 2-phenylpropyl-(2)-oxycarbonyl, 2-(4-biphenyl)propyl-(2)-oxycarbonyl, 2-nitrophenylsulfenyl and diphenylphosphinyl.

31. The compound of claim 26, wherein $R_7$ is selected from the group consisting of hydrogen and $OR_{11}$, wherein $R_{11}$ is a chemical protecting group.

32. The compound of claim 31, wherein said $R_{11}$ protecting group is selected from the group consisting of lower aryl and alkylether.

33. The compound of claim 32, wherein said $R_{11}$ protecting group is selected from the group consisting of, triphenylmethyl, acetal, tetrahydropyranyl, silyl ether, trimethylsilyl and t-butyl-dimethylsilyl.

34. The compound of claim 32, wherein said $R_{11}$ protecting group is selected from the group consisting of hydroxylic and amino groups.

35. The compound of claim 26, wherein $R_8$ is selected from the group consisting of lower and heterocyclic alkyl.

36. The compound 35, wherein $R_8$ is selected from the group consisting of methyl, isopropyl, morpholino, pyrrolidino and 2,2,6,6-tetramethylpyrrolidino.

37. The compound of claim 26, wherein $R_{12}$ is a phosphate protecting group.

38. The compound of claim 37, wherein said phosphate protecting group is selected from the group consisting of trichloroethyl, allyl, cyanoethyl and sulfonylethyl.

39. A method of synthesizing a compound of a structure selected from the group consisting of:

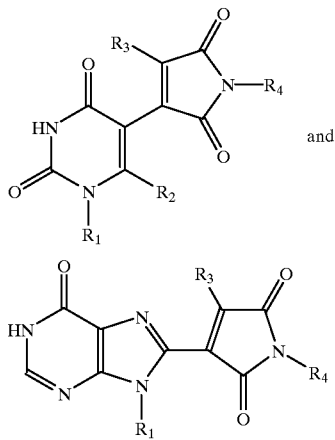

wherein:

$R_1$, $R_2$, $R_3$ and $R_4$ are each independently a derivatizing group, including hydrogen, the method comprising the steps of contacting a derivatized base with mercuric acetate and condensing with N-alkylmaleimide.

40. A method of synthesizing a compound of a structure selected from the group consisting of:

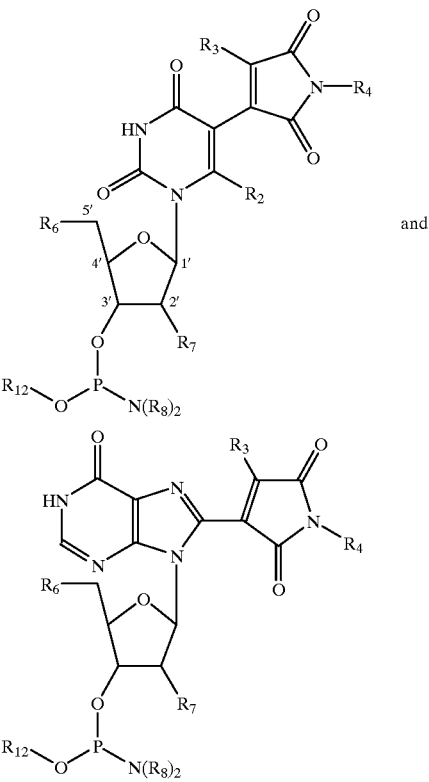

wherein $R_2$, $R_3$, $R_4$, $R_6$, $R_7$, $R_8$ and $R_{12}$, are each independently a derivatizing group, including hydrogen, the method comprising the steps of:

(a) contacting a nucleoside with mercuric salt, followed by condensation with N-alkylmaleimide;

(b) protecting amino groups of said nucleoside with a protecting group;

(c) protecting a 5' hydroxyl of said nucleoside with an acid labile group; and (d) condensing with allylic phosphoramidate reagent.

* * * * *

SEQUENCE LISTING (1) GENERAL INFORMATION:

(iii) NUMBER OF SEQUENCES:1

(2) INFORMATION FOR SEQ ID NO:1:

(i) SEQUENCE CHARACTERISTICS:
      (A) LENGTH:23
      (B) TYPE:nucleic acid
      (C) STRANDEDNESS:single
      (D) TOPOLOGY:linear (ix) FEATURE:
      (D) OTHER INFORMATION: Wherein N is 2'-deoxy,
         5-maleimidouridine (xi) SEQUENCE DESCRIPTION: SEQ ID NO:1:

NCCACTACAC CTACTATCCA TTA                   23